US007396689B2

United States Patent
Dowd et al.

(10) Patent No.: US 7,396,689 B2
(45) Date of Patent: Jul. 8, 2008

(54) METHOD OF ADJUSTING THE WORKING RANGE OF A MULTI-ANALYTE ASSAY

(75) Inventors: Roger Dowd, Natick, MA (US); Jeffrey G. Donahue, Hopkinton, MA (US)

(73) Assignee: Decision Biomarkers Incorporated, Waltham, MA (US)

( * ) Notice: Subject to any disclaimer, the term of this patent is extended or adjusted under 35 U.S.C. 154(b) by 3 days.

(21) Appl. No.: 11/221,198

(22) Filed: Sep. 6, 2005

(65) Prior Publication Data

US 2006/0177873 A1 Aug. 10, 2006

Related U.S. Application Data

(60) Provisional application No. 60/650,324, filed on Feb. 4, 2005.

(51) Int. Cl.
 *G01N 33/543* (2006.01)
(52) U.S. Cl. ................... 436/518; 435/7.1; 435/7.92
(58) Field of Classification Search ............. 435/6, 435/7.1, 7.92–7.94, 962, 973; 436/501, 518, 436/164, 823, 962, 973
See application file for complete search history.

(56) References Cited

U.S. PATENT DOCUMENTS

| | | | |
|---|---|---|---|
| 4,743,542 A | 5/1988 | Graham, Jr. et al. |
| 5,028,535 A | 7/1991 | Buechler et al. |
| 5,089,391 A | 2/1992 | Buechler et al. |
| 5,356,784 A | 10/1994 | Kauvar |
| 5,356,785 A | 10/1994 | McMahon et al. |
| 5,468,648 A | 11/1995 | Chandler |
| 5,480,792 A | 1/1996 | Buechler et al. |
| 5,521,102 A | 5/1996 | Boehringer et al. |
| 5,541,069 A | 7/1996 | Mortensen et al. |
| 5,552,276 A | 9/1996 | Mochida et al. |
| 5,607,863 A | 3/1997 | Chandler |
| 5,620,901 A | 4/1997 | Kauvar |
| 5,679,526 A | 10/1997 | Buechler et al. |
| 5,710,005 A | 1/1998 | Rittenburg |
| 5,770,460 A | 6/1998 | Pawlak et al. |
| 5,780,308 A | 7/1998 | Ching et al. |
| 5,846,838 A | 12/1998 | Chandler |
| 5,869,345 A | 2/1999 | Chandler |
| 5,874,216 A | 2/1999 | Mapes |
| 5,877,028 A | 3/1999 | Chandler et al. |
| 5,879,951 A | 3/1999 | Sy |
| 5,939,252 A | 8/1999 | Lennon et al. |
| 5,939,272 A | 8/1999 | Buechler et al. |
| 5,962,339 A | 10/1999 | Midgely |
| 5,968,839 A | 10/1999 | Blatt et al. |
| 5,985,579 A | 11/1999 | Buechler et al. |
| 6,027,904 A | 2/2000 | Devine et al. |
| 6,030,770 A | 2/2000 | Brust |
| 6,086,748 A | 7/2000 | Durst et al. |
| 6,136,610 A | 10/2000 | Polito et al. |
| 6,140,134 A | 10/2000 | Rittenburg |
| 6,177,281 B1 | 1/2001 | Manita |
| 6,180,340 B1 | 1/2001 | Nelson |

(Continued)

FOREIGN PATENT DOCUMENTS

CA 2069833 AA 11/1992

(Continued)

OTHER PUBLICATIONS

U.S. Appl. No. 09/949,756, filed Sep. 12, 2001, Fitzgerald et al.

*Primary Examiner*—Long V. Le
*Assistant Examiner*—Gary W Counts
(74) *Attorney, Agent, or Firm*—Leslie Meyer-Leon; IP Legal Strategies Group P.C.

(57) ABSTRACT

The invention features a method of adjusting the concentration of at least one but not all of a plurality of analytes in a fluid sample to match a known working range of detection of an analyte assay system, where each of the plurality of analytes may or may not be present within an expected initial concentration range having a high end and a low end, and at least one analyte has a high end expected concentration range that exceeds the high end of the working range of the assay system. The expected concentration of the high concentration analyte is adjusted by a proportional scaling constant, $\alpha$, so that the high end of the adjusted expected concentration range is less than or equal to the high end of the working range, without adjusting the expected concentration range of at least one other of the plurality of analytes. Adjustment is preferably accomplished by adding to the solution phase of the assay one or more scaling agents, each scaling agent binding with specificity to an analyte and thereby preventing it from being detected by the assay system, e.g., by competing with binding to immobilized capture agent. This scaling method contrasts with prior methods, in which a concentration of available analyte is offset by a fixed amount to adjust the detectable threshold of the assay. Here, the amount of scaling agent is proportional to a scaling coefficient, and the scaling agent is present in the solution phase of the assay at high concentrations relative to analyte. Due to the equilibrium conditions established by the laws of mass transfer, the amount of free analyte remaining in solution in the presence of scaling agent is predictable and finite, and can be measured as a quantitative indicator of the initial concentration of the analyte in the sample.

19 Claims, 16 Drawing Sheets

U.S. PATENT DOCUMENTS

| | | |
|---|---|---|
| 6,218,134 B1 | 4/2001 | Yamauchi et al. |
| 6,284,472 B1 | 9/2001 | Wei et al. |
| 6,316,205 B1 | 11/2001 | Guan et al. |
| 6,329,209 B1 * | 12/2001 | Wagner et al. ............ 436/518 |
| 6,410,341 B1 | 6/2002 | Freitag et al. |
| 6,475,805 B1 | 11/2002 | Charm et al. |
| 6,498,010 B1 | 12/2002 | Fitzgerald et al. |
| 6,509,196 B1 | 1/2003 | Brooks et al. |
| 6,551,788 B1 | 4/2003 | Bell |
| 6,582,970 B1 | 6/2003 | Manita |
| 6,617,116 B2 | 9/2003 | Guan et al. |
| 6,656,744 B2 | 12/2003 | Pronovost et al. |
| 6,670,196 B1 | 12/2003 | Buechler |
| 6,680,209 B1 | 1/2004 | Buechler et al. |
| 6,696,243 B2 | 2/2004 | Siiman |
| 2002/0086337 A1 | 7/2002 | Fitzgerald et al. |
| 2003/0054571 A1 | 3/2003 | Watkins et al. |
| 2003/0078737 A1 | 4/2003 | Kays et al. |
| 2005/0112585 A1 | 5/2005 | Zlchl et al. |

FOREIGN PATENT DOCUMENTS

| | | |
|---|---|---|
| EP | 0516095 A2 | 2/1992 |
| EP | 0690306 A1 | 3/1996 |
| JP | 4351962 A2 | 12/1992 |
| WO | WO 94/23298 | 10/1994 |
| WO | WO 99/04267 | 1/1999 |
| WO | PCT/US2006/003737 | 11/2006 |

* cited by examiner

K=2E-9

US 7,396,689 B2

METHOD OF ADJUSTING THE WORKING RANGE OF A MULTI-ANALYTE ASSAY

REFERENCE To PRIOR APPLICATION

This application is based on and claims priority from U.S. Provisional Patent Application Ser. No. 60/650,324, filed Feb. 4, 2005, which is hereby incorporated by reference.

FIELD OF THE INVENTION

This invention relates to methods for using multiplexed immunoassays to quantify simultaneously the concentration of multiple analytes in a liquid sample.

BACKGROUND OF THE INVENTION

Practical immunodiagnostic tests for in vitro detection of analytes in fluid samples are highly specific but vary in speed, sensitivity, and the degree to which they are qualitative or quantitative. They also vary widely in assay methods used, from solution based assays to those that are formulated on solid supports, such as beads, membranes, lateral flow strips, microtiter plates, biochips, and planar or semi-planar substrates such as coated slides. Quantitative immunoassays are usually associated with automated platforms designed to run high-throughput assays in a clinical environment. These systems are typically designed to measure a single analyte for each sample-test. Other assay methods such as ELISA plate and lateral flow assay can also be automated but are limited in the ability to multiplex.

Common methods used for inexpensive, qualitative testing are the dipstick and lateral flow strip formats. These assays are also typically designed to test for a single, or at most only a few, analytes per assay. Such test devices are usually designed to produce a visual signal on the solid support that can be observed by the naked eye, providing only a qualitative, or at best a semi-quantitative, test result. The sensitivity of the lateral flow format is generally maximized by increasing the strength of the visible signal, which decreases the lower limit of detection of the assay (LLD). In some cases, however, optimizing the visual signal creates an assay that is too sensitive, because the assays detect a concentration of analyte below the desired detection level, thereby leading to false positives. The sensitivity of the assay no-longer matches the concentration range over which one wishes to detect the analyte. In such cases, lateral flow assays have been adjusted by adding small increments of adjustment antibodies to offset the signal, so that a positive test signal is only observed when the analyte is present at or above a predetermined threshold.

A new generation of immunoassays is being developed to better meet the needs of clinicians and researchers. Multiplexed immunoassays are designed to measure multiple (e.g., as high as 42 or more) analytes in a single-sample test. These assays provide the potential to reduce costs and minimize sample volumes in certain volume-sensitive applications. Sample volume requirement is reduced by measuring a number of analytes in a single sample. Examples of sample-limited applications include pediatric testing in diagnostics, animal model testing in research, and the screening of serum banks to develop disease-specific biomarkers. In each of these cases, the volume of sample available for testing is limited. Microarray technology provides a promising platform for assaying multiplexed immunoassays that can potentially provide more sensitive and quantitative methods for measuring the concentration of multiple analytes within a single assay. The term "microarray" refers to a solid, planar or semi-planar substrate on which are arranged a set of microscopic spatially distinct areas, or spots, to which are attached one or more capture molecules. The intensity of the signal resulting from the assay is quantified using an optical imager.

Two parameters that are often used to describe the capability of a microarray assay are the lowest level of detection (LLD) and the working range. The LLD is the lowest analyte concentration that can be reliably quantified in the assay, and is a measure of the sensitivity of the assay. The working range, also variously referred to as the dynamic range or the assay range, is the range of analyte concentrations over which a change in concentration can be reliably measured, usually the range over which the optical signal is a linear function of analyte concentration. By way of example, an assay for the cytokine IL-8 having an LLD of 10 pg/mL and a working range of three logs provides a reliable quantitative measure of concentrations between 10 pg/mL and 10 ng/mL, but would not be acceptable to a researcher who is interested in IL-8 over a range of 500 pg/mL to 50 ng/mL. The assay would have adequate sensitivity at the low end of the working range (10 pg/mL), but would not discriminate IL-8 concentrations above 10 ng/mL and therefore would not meet the high-end requirements.

When a single analyte assay is too sensitive, the sample can be diluted to adjust the expected analyte range to the assay range. Dilution techniques are not suitable, however, in the case of a multiplexed immunoassay, which attempts independent, simultaneous measurement of multiple analytes in a single sample. By way of example, consider a simple two-plex immunoassay (two antigenic proteins detected in a single sample) having a working range of 10 pg/mL to 10 ng/mL for both analytes. Consider the application of this assay for detecting IL-7 over the range of 20 pg/mL to 2 ng/mL, and detecting IL-8 over the range of 500 pg/mL to 50 ng/mL. The working range of the assay is well suited to detect the target range of concentration for IL-7, but the targeted IL-8 concentration exceeds the upper end of the working range. Were the sample to be diluted (e.g., by 1:5), the IL-8 would be within the working range, but the IL-7 concentration would be below the low end of the assay working range (FIG. 1). The situation is further exacerbated when the number of analytes tested is increased to 10, 20 or higher. Thus, simple dilution methods do not have enough degrees of freedom to adjust the working range of the assay independently for each analyte in a multiplexed assay. What is needed is a method to independently match the range of each analyte to the assay range in a multiplexed immunoassay, preferably over several orders of magnitude, preferably over a range of three, four, five or six orders of magnitude.

SUMMARY OF THE INVENTION

The invention features a method of varying the sensitivity of a multi-analyte assay for individual analytes over several orders of magnitude, by adjusting the working range of a multi-analyte immunoassay for one of a plurality of analytes to be detected, without altering the low detection limit (LLD) and/or the working range of the assay for the remaining analytes. This is accomplished by adding to the solution phase of the assay one or more scaling agents, which are molecules that block the availability of a fraction of the target analyte by occupying the binding site, e.g., an epitope, on those analytes that are specifically bound by the capture molecule. In contrast to prior-art assays in which low concentrations of antibody relative to antigen are used to offset the concentration of available antigen by a fixed amount (referred to herein as "offset assays"), the scaling agent of the invention is present in high concentrations relative to analyte concentrations. The effect is to reduce the available analyte concentration by a fractional amount corresponding to a constant, referred to herein as a scaling coefficient ($\alpha$) The residual amount of analyte remaining as free analyte is the quantity of analyte that is then measured. Thus, the scaling method of the invention is further distinct from prior offset assay methods in that, in the case of offsetting, the residual amount of free-floating antibodies is treated as an error and usually ignored. In the case of scaling, the residual amount of free-floating antigen is the quantity to be measured and thus exploited.

It is therefore the goal of the invention to vary the sensitivity and working range for one or more analytes in a sample independently using a controllable parameter that can discriminate between the analytes in the assay. The assay quantitatively determines the concentration of a plurality of analytes in a liquid sample in which each of said plurality of analytes is characterized by one or more assay parameters including without limitation low detection limit (LLD) and working range. The assay is based on a method which includes contacting the sample with a specifically selective binding reagent (e.g. ligands), preferably a capture reagent bound to a solid support, each of the ligands characterized in that it reversibly binds an analyte which is or may be present in the liquid sample to form an analyte/ligand complex, and in that it is specific for the analyte as compared to any other components which are or may be present in the liquid sample. Prior to or together with such contact with a capture agent, the sample is allowed to contact an amount of a first scaling agent which has a binding specificity for a first analyte of the plurality of analytes. Binding between the first scaling agent and the first analyte inhibits binding of a sub-population of the first analyte with its corresponding capture agent. Binding by the first scaling agent to the first analyte changes one or more assay parameters for the first analyte independent of the assay parameters for other analytes in the sample; that is, the scaling agent does not change an assay parameter for at least one other of the plurality of analytes.

The analyte to be detected is a compound, composition, aggregation, or other substance that can be specifically captured from a complex mixture of compounds, compositions and aggregations. That is, the analyte, or portion thereof, will be antigenic or haptenic having at least one determinant site, or will be a member of a naturally-occurring binding pair, e.g., carbohydrate and lectin, hormone and receptor, complementary nucleic acids, and the like. Analytes of particular interest include antigens, antibodies, proteins, carbohydrates, haptens, drugs, hormones, hormone metabolites, macromolecules, toxins, bacteria, viruses, enzymes, tumor markers, nucleic acids, and the like, although other types of substances may also be detected.

The term "scaling agent" as used herein is intended to include all substances which are able to bind the analyte, either directly (i.e., without an intermediate binding substance) or indirectly (i.e., with one or more intermediate binding substances forming a linkage). Preferably, the scaling agent is a specific binding substance capable of binding directly or indirectly to the analyte with a high affinity, typically being at least about $10^7$ $M^{-1}$, usually being at least about $10^9$ $M^{-1}$, sometimes being $10^{10}$ $M^{-1}$, and optimally being $10^{11}$ $M^{-1}$ or $10^{12}$ $M^{-1}$ or greater. The scaling agent should be free from cross-reactivity with other substances that may be present in the sample or in an assay reagent. Preferably, the association between the scaling agent and analyte, e.g., when the analyte is an antigen, is based on highly specific noncovalent interactions between the antigenic determinant, or epitope, of the antigen and the variable-region domain of an antibody molecule used as the scaling agent. The scaling agent can be a monoclonal or polyclonal antibody raised against the analyte. Alternatively, the scaling agent can be a natural receptor for a biological analyte, an aptomer, or another molecule harvested or engineered for the purpose of specifically binding to an analyte. In cases where the analyte is itself an antibody, antigens or haptens recognized by the antibody can be used as the scaling agent of the invention.

The present invention is useful in assaying for a wide variety of analytes in virtually any type of sample which can be provided in a fluid form. Especially suitable are biological specimens, such as blood, serum, plasma, urine, cerebral fluid, spinal fluid, ocular lens liquid (tears), saliva, sputum, semen, cervical mucus, scrapings, swab samples, and the like. In addition, the method is suitable for industrial, environmental and food samples, such as water, reservoirs, process streams, milk, meat, poultry, fish, conditioned media, and the like. Under certain circumstances, it may be desirable to pre-treat the sample, such as by suspending in fluid, separation, dilution, concentration, filtration, chemical treatment, or a combination thereof, in order to improve the compatibility of the sample with the remaining steps of the assay. The selection and pretreatment of biological, industrial, and environmental samples prior to immunological testing is well known in the art.

Categories of immunoassays include direct and indirect competitive assays, and non-competitive assays such as sandwich assays. A competitive assay relies on competition for binding to a specific binding agent between a known amount of labeled analyte and an unknown amount of analyte in the sample. The more analyte that is present in the sample, the less binding agent available to bind to a competing analyte or analyte-analogue. In a sandwich assay, a binding agent is immobilized on a solid support to serve as a capture agent. Analyte in the test sample is allowed to react with the binding agent on the support. After the support is washed, a second, detectable agent that binds specifically to a different epitope on the analyte is added and allowed to react with the captured analyte, thereby becoming "sandwiched" between the detectable binding agent and the immobilized binding agent. After any excess detectable binding agent is washed away, observations are made of detectable binding agent bound to the sandwich complex. The observed signal is directly proportional to the amount of antigen in the test sample.

Accordingly, in one aspect, the invention features a method of adjusting the concentration of at least one but not all of a plurality of analytes in a fluid sample to match a working range of detection of an analyte assay system. The method includes the steps of a) obtaining characterization of a working range of detection of an analyte assay system for quantitative determination of the concentration of a plurality of analytes in a fluid sample, the characterization including a high end and a low end of the working range; b) providing a fluid sample in which each of a plurality of analytes may or may not be present within an expected initial concentration range having a high end and a low end, the plurality of analytes including at least one high concentration analyte having a high end expected concentration range that exceeds the high end of the working range of the assay system; and c) adjusting the expected concentration of the high concentration analyte by a proportional scaling constant, $\alpha$, so that the high end of the adjusted expected concentration range is less than or equal to the high end of the working range, without adjusting the expected concentration range of at least one other of the plurality of analytes. The ratio of the adjusted concentration of the high concentration analyte to the initial concentration of the high concentration analyte can be independent of the initial concentration of the high concentration analyte.

As discussed above, one manner of adjusting the expected concentration of the high concentration analyte is by a) providing a scaling agent (S) having binding specificity for at least one, but not all, of the plurality of analytes, whereby binding of analyte by the scaling agent prevents detection of the analyte by the assay system; and b) introducing a certain amount of the scaling agent (S) to the sample to create a reaction mixture, under conditions such that, subsequent to the reaction mixture coming substantially to equilibrium binding conditions, the reaction mixture includes a scaling agent-analyte complex portion having a scaling agent-analyte complex concentration ([AS]), a free analyte portion having a free analyte concentration ([$A_f$]), and a free scaling agent portion having a free scaling agent concentration ([$S_f$]), wherein the introducing results in a total scaling agent concentration ([$S_T$]) in the reaction mixture is equal to the sum of the free scaling agent concentration plus the scaling agent-analyte complex concentration ([$S_f$]+[AS]), and a total analyte concentration ([$A_T$]) in the reaction mixture equal to the sum of the free analyte concentration plus the scaling agent-analyte complex concentration ([$A_f$]+[AS]). The total concentration of scaling agent [$S_T$] is preferably greater than or equal to the high end expected initial concentration of the high concentration analyte in the reaction mixture. [$S_T$] can be at least four times greater than [$A_f$] and the product of [$A_f$] and $K_a$ is less than one fourth. In some embodiments, [$S_T$] is at least nine times greater than [$A_f$] and the product of [$A_f$] and $K_a$ is less than one ninth. It is understood that "equal to", as used herein, refers to concentrations that that approach equality, and are thus approximately equal.

In one embodiment, the scaling agent can be introduced to the sample in solution form, in which case the concentrations of analyte, scaling agent, and scaling agent, complex is a function of the volume of reaction mixture resulting from the combined fluid sample and reagents. Another option is to add the scaling agent as a dry reagent, particularly in the context of an assay conducted in a biochip.

In some embodiments, the method of the invention can further include introducing the sample to a solid support including at least one immobilized capture agent, the capture agent having binding specificity for at least one of the plurality of analytes, under conditions permitting binding between the analytes and the capture agent to form analyte-capture agent complex, and determining the analyte-capture agent complex on the solid support as an indication of the initial concentration of the analytes in the fluid sample. Binding of the scaling agent to the high concentration analyte prevents binding of the high concentration analyte to the at least one capture agent. The fluid can be introduced to the solid support prior to adjusting the expected concentration of the high concentration analyte. Another option is to adjust the expected concentration of the high concentration analyte prior to introducing the fluid sample to the solid support, or the adjusting step can coincide with introducing the fluid sample to the solid support.

Preferably, the ratio of the adjusted concentration of the high concentration analyte to the initial concentration of the high concentration analyte is independent of the initial concentration of the high concentration analyte.

Preferably, where the scaling agent binds the high concentration analyte with a binding affinity $K_a$, and [$S_T$] is greater than [$A_T$], the scaling constant, $\alpha$, is proportional to, or in some cases equals, ($K_a$[$S_T$]+1). Under these conditions, the ratio of the free analyte concentration to the total analyte concentration, ([$A_f$]/[$A_T$]), is independent of the total analyte concentration ([$A_T$]) at the total scaling agent concentration ([$S_T$]) and is independent of the total analyte concentration within the adjusted concentration range.

The amount of analyte-capture agent complex on the solid support can be determined by measuring a parameter representative of the amount of each analyte bound to the capture agent as an indication of the initial concentration of the analyte in the sample. This can involve measuring a detectable signal bound to the support. By way of example, one or more detection binders can be introduced to the solid support under conditions permitting the detection binder to bind the analyte-capture agent complex. The amount of detection binder bound to the analyte-capture agent complex is an indication of the initial concentration of the analytes in the fluid sample. Where the detection binder includes a detectable signal, the amount of detection binder bound to the analyte-capture agent complex is determined by measuring the detectable signal, the signal being proportional to the concentration of the analyte in the sample.

In some embodiments, the scaling agent-analyte complex can be removed from the reaction mixture prior to contacting the reaction mixture with a solid support.

In other embodiments, e.g., where the assay system is a competitive assay, the method further includes the step of, prior to introducing the sample to the solid support, introducing to the reaction mixture an analyte analogue conjugate that is capable of competing with the high concentration analyte for binding to the scaling agent and the capture agent. Preferably, the analyte analogue conjugate bears a detectable label and/or emits a detectable signal. In such assays, one determines the amount of each of the analytes bound to the at least one capture agent by determining the amount of analyte analogue conjugate bound to the solid support, as an inverse indication of the amount of the corresponding analyte bound to the solid support, and as an inverse indication of the initial concentration of the corresponding analytes in the fluid sample.

Where the analyte analogue conjugate is present in the reaction mixture at a total analyte analogue conjugate concentration [$A^*_T$], the total scaling agent concentration [$S_T$] should be greater than or equal to a sum of the total analyte concentration and the total analyte analogue conjugate concentration ([$A_T$]+[$A^*_T$]).

Preferably, the total scaling agent concentration ([$S_T$]) is at least four times greater than a sum of the free analyte concentration and the free analyte analogue conjugate concentration ([$A_f$]+[$A^*_f$]), and the product $K_a$ ([$A_f$]+[$A^*_f$]) is less than one fourth. In some embodiments, the total scaling agent concentration ([$S_T$]) is at least nine times greater than the sum of the free analyte concentration and the free analyte analogue conjugate concentration ([$A_f$]+[$A^*_f$]), and the product $K_a$ ([$A_f$]+[$A^*_f$]) is less than one ninth.

In another aspect, the invention features a method of measuring the affinity of a binding agent, $K_a$, for an analyte, the method including the steps of a) providing a fluid sample including an analyte; b) experimentally determining a value of a scaling constant $\alpha$; and c) calculating $K_a$, where $K_a$ is equal to ($\alpha-1$)/[$S_f$].

The invention further includes an apparatus for performing an assay for the quantitative determination of the concentration of a plurality of analytes in a fluid sample, the assay system including a defined working range having a high end and a low end. The apparatus includes a) means for providing a fluid sample in which each of a plurality of analytes which may or may not be present within an expected initial concentration range having a high end and a low end, the plurality of analytes including at least one high concentration analyte having a high end expected concentration range that exceeds the high end of the working range of the assay system; b) means for adjusting the expected concentration of the high concentration analyte by a proportional scaling constant, $\alpha$, so that the high end of the adjusted expected concentration range is less than or equal to the high end of the working range, without adjusting the expected concentration range of at least one other of the plurality of analytes; c) means for introducing the sample to a solid support including at least one immobilized capture agent, the capture agent having binding specificity for at least one of the plurality of analytes, under conditions permitting binding between the analytes and the capture agent to form analyte-capture agent complex; and d) means for determining the analyte-capture agent complex on the solid support as an indication of the initial concentration of the analytes in the fluid sample. The adjusting means can include means for introducing a certain amount of the scaling agent (S) to the sample to create a reaction mixture, under conditions such that, subsequent to the reaction mixture coming substantially to equilibrium binding conditions, the reaction mixture including a scaling agent-analyte complex portion having a scaling agent-analyte complex concentration ([AS]), a free analyte portion having a free analyte concentration ([$A_f$]), and a free scaling agent portion having a free scaling agent concentration ([$S_f$]); wherein the introducing results in a total scaling agent concentration ([$S_T$]) in the reaction mixture equal to the sum of the free scaling agent concentration plus the scaling agent-analyte complex concentration ([$S_f$]+[AS]), and a total analyte concentration ([$A_T$]) in the reaction mixture equal to the sum of the free analyte concentration plus the scaling agent-analyte complex concentration ([$A_f$]+[AS]) and wherein the scaling agent (S) having binding specificity for at least one, but not all, of the plurality of analytes.

The means for determining the analyte-capture agent complex on the solid support can include means for measuring a parameter representative of the amount of each analyte bound to the capture agent as an indication of the initial concentration of the analyte in the sample. Preferably, the means for determining the analyte-capture agent complex on the solid support includes means for measuring a detectable signal. The means for determining the analyte-capture agent complex on the solid support can also include means for introducing at least one detection binder to the solid support under conditions permitting the detection binder to bind the analyte-capture agent complex, and means for determining the amount of detection binder bound to the analyte-capture agent complex as an indication of the initial concentration of the analytes in the fluid sample, such as, e.g., means for measuring the detectable signal, the signal being proportional to the concentration of the analyte in the sample.

In some situations the apparatus can further include optional means for removing the scaling agent-analyte complex from the reaction mixture prior to the contacting the reaction mixture with a solid support.

The apparatus can further include means for introducing to the reaction mixture an analyte analogue conjugate including a detectable signal, the analogue conjugate capable of competing with the high concentration analyte for binding to the scaling agent and the capture agent. Here, the apparatus can further include means for determining the amount of analyte analogue conjugate bound to the solid support as an inverse indication of the amount of analyte bound to the solid support, and as an inverse indication of the initial concentration of the analytes in the fluid sample.

BRIEF DESCRIPTION OF THE DRAWINGS

FIG. 15 illustrates the effect of adding $15 \times 10^{-9}$ mol/L anti-IL-1B as a scaling agent on the response of the assay to the three antigens IL-1B, IL-2, and TNFα.

FIG. 16 illustrates the effect of adding $15 \times 10^{-9}$ mol/L anti-IL-1B as a scaling agent on the response of the assay to the three antigens IL-1B, IL-6, and IL-7.

DETAILED DESCRIPTION OF THE INVENTION

Figure 1:
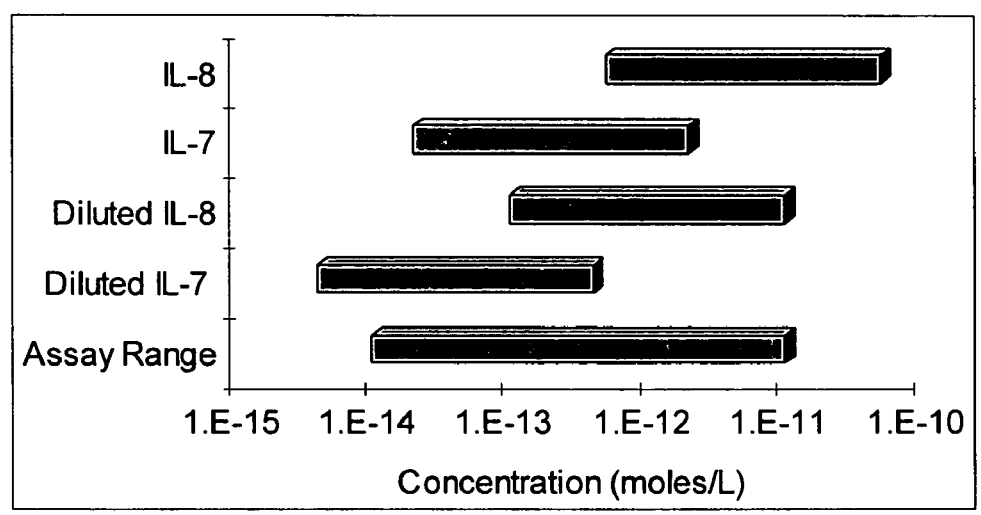
FIG. 1 is a bar graph illustrating, for a hypothetical assay, the range of IL-7 and IL-8 concentrations in the original sample as compared to in a diluted sample and to the working range of a two-plex assay.

Scaling an assay involves altering the LLD and working range of an assay. It is often the case with quantitative binding assays, e.g., immunoassays that the working range of quantification is not matched to the expected range of analyte. For multiplexed assays it is advantageous to scale the sensitivity and working range for one or more analytes without affecting the sensitivity and working range of the assay for other analytes in the sample. Scaling agents are added to reduce the proportion of a particular analyte in the sample, thereby reducing the effective concentration of that analyte by a constant scaling coefficient.

Accordingly, the invention relies on binding a specified amount of the analyte present in the sample by pre-exposing the sample to a scaling agent, which is a molecule having a high binding affinity for the analyte, preferably an antibody or receptor having high specificity for the target analyte to be scaled. The scaling agent binds to a portion of the analyte in the sample, and the amount of scaling agent used is equal to or in excess of a scaling coefficient that can be determined either theoretically or experimentally. Due to the equilibrium nature of association and dissociation between scaling agent and analyte in solution, the sample can be expected to maintain a finite amount of unbound, i.e., free, analyte, which is then readily detectable in the subsequent detection phase of the assay.

Preferably, the amount of scaling agent added to the sample is selected to be equal to or greater than that required to elicit a transition between a scaling portion of a partition curve and an offset portion of the partition curve, as further defined below.

In operation, the first step of the assay of the invention includes reacting a sample suspected of containing the analyte with a certain amount of the scaling agent, the certain amount selected to reduce the amount of available free analyte in the reacted sample according to a constant scaling coefficient. The scaling agent is exposed to the sample during the course of a pre-treatment step prior to introducing the assay sample to the median, device, or solid support bearing the capture agent. The scaling agent can be introduced in a suitable buffer or other liquid carrier, which is combined with the sample to form a liquid reaction phase and allowed to reach equilibrium. Alternatively, the scaling agent can be introduced on a solid phase (such as particles, beads, a dipstick, an agarose gel, or the like) which is combined with the liquid sample and permitted to reach equilibrium solution conditions. In a third alternative, the scaling agent can be bound to the interior of a transfer pipette, a filter, or a pre-treatment chamber or well used to introduce the sample to the test device, as long as the scaling agent reaches equilibrium in the sample prior to exposure to capture agent. The reaction between the sample and the scaling agent is allowed to proceed to equilibrium prior to any subsequent assay steps, usually proceeding for at least about ten seconds, more usually requiring at least one to two minutes. The time required for the scaling phase of the assay to reach equilibrium varies according to temperature and solution conditions of the medium and the strength of affinity of the scaling agent for the analyte, and can be minimized by use of scaling agents with maximum binding affinity. Preferably, the solution conditions of the assay are determined so as to assure sufficient and consistent binding conditions between scaling agent and analyte prior to performing subsequent steps of the assay.

After the reaction between the scaling agent and sample has been allowed to reach equilibrium, the steps of the detection phase of the assay are initiated, usually without separating the analyte/scaling agent complex from the reaction phase. The reacted sample is then contacted with a capture agent in the detection phase of the assay. Preferably the capture agent is immobilized on a solid support, most preferably a capture agent fixed to a microarray formatted support. In this way, residual free analyte remaining in the reaction phase (i.e., analyte that is not bound to scaling agent) binds to the capture agent on the solid support.

The degree to which a scaling agent adjusts the working range of the assay for a given analyte depends primarily on the binding affinity of the scaling agent for the analyte (taking into account the number of epitopes on the analyte that are recognized by the scaling agent) and the concentration of the scaling agent in relation to antigen concentration. For the purposes of simplifying discussion herein, the amount of scaling agent used to adjust the working range of the detection assay is best modeled by the case of a sandwich immunoassay system in which the scaling agent is an antibody, the analyte is an antigen, and there is a one-to-one binding association between antigen (Ag) and antibody (Ab) per antibody/antigen (AbAg) complex. It is within the understanding of those skilled in the art to adjust this model to accommodate multi-epitope analytes, higher binding ratios, and alternative types of complimentary scaling agent/analyte pairs.

The dynamics of the method of the invention can be modeled according to the laws of mass action, which are predictable, quantifiable and can thus be exploited to tailor an immunoassay for a particular analyte. The relative concentrations of free antibody [Ab], free antigen [Ag], and antibody/antigen complex [AbAg] in a reaction mixture at equilibrium are defined by Equation (1).

$$K_a = \frac{[AbAg]}{[Ab] \cdot [Ag]} \quad (1)$$

where, $K_a$ = the antibody-antigen association constant (L/mol)

[AbAg] = the molar concentration of AbAg complexes at equilibrium,

[Ab] = the molar concentration of antibody at equilibrium, and

[Ag] = the molar concentration of antigen at equilibrium.

The affinity constant, $K_a$, is characteristic of a given antibody. Low-affinity antibodies have $K_a$ values between $10^7$ to $10^9$ L/mol; high-affinity antibodies have $K_a$ values as high as $10^{11}$ L/mol/or even $10^{12}$ L/mol.

Assuming a one-to-one correspondence of antibody to antigen in the AbAg complex, the initial antigen concentration $[Ag_i]$ is equal to the equilibrium free analyte concentration [Ag] plus the equilibrium concentration of the antibody/antigen complex [AbAg] according to Equation (2). Similarly, the initial antibody concentration $[Ab_i]$ is equal to the equilibrium free antibody concentration [Ab] plus the equilibrium concentration of [AbAg] complex according to Equation (3).

$$[Ag_i] = [Ag] + [AbAg] \quad (2)$$

$$[Ab_i] = [Ab] + [AbAg] \quad (3)$$

Equations (1), (2) and (3) can be combined to show that the concentration of free antigen at equilibrium is a function of the antibody affinity constant and the initial concentrations of antibody and antigen, according to Equation (4).

$$[Ag] = \frac{-\left([Ab_i] - [Ag_i] + \frac{1}{K_a}\right) + \sqrt{\left([Ab_i] - [Ag_i] + \frac{1}{K_a}\right)^2 + \frac{4[Ag_i]}{K_a}}}{2} \quad (4)$$

where:

$[Ag_i]$ = the initial molar concentration of antigen (mol/L), an $[Ab_i]$ = the initial antibody concentration (mol/L).

Figure 2:
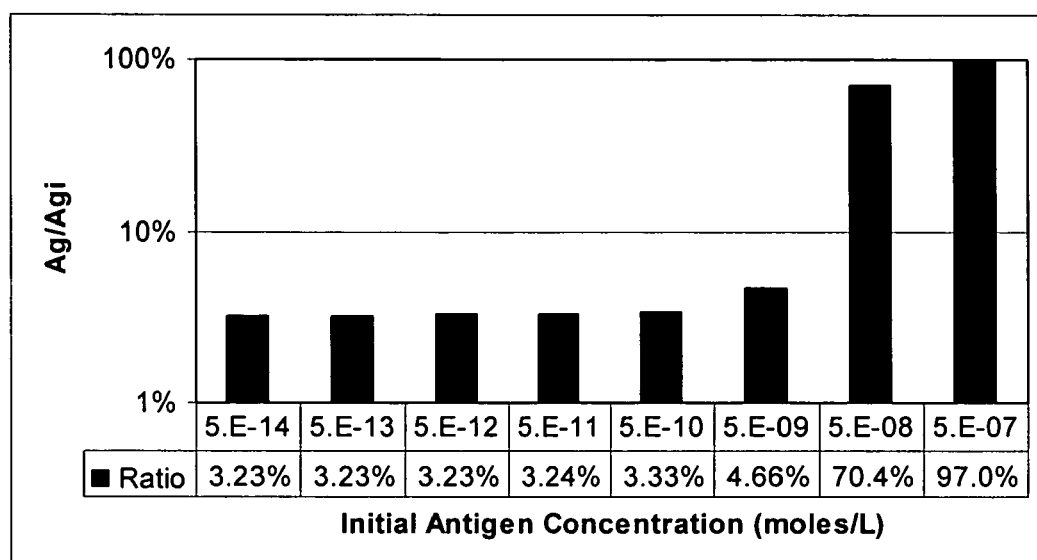
FIG. 2 is a bar graph illustrating the ratio of available antigen concentration to initial antigen concentration over a $10^8$ range in initial antigen concentration. The data shown in FIG. 2 is calculated based on assays run with an initial antigen concentration range of $0.05\text{-}500{,}000 \times 10^{-12}$ mol/L, an initial scaling antibody concentration of $15 \times 10^{-9}$ mol/L, and a binding affinity of $2 \times 10^9$ L/mol. Numerical ratios are listed below the chart.

Equation (4) can be used to examine the ratio of free antigen to initial antigen over a range of initial antigen concentrations and in the presence of a fixed concentration of soluble antibody (FIG. 2). FIG. 2 is a bar graph of the ratio of free antigen to initial antigen expected over an initial antigen concentration range of 0.05-500,000×10$^{-12}$ mol/L, and in the presence of an initial soluble antibody concentration of 15×10$^{-9}$ mol/L. The antibody has a binding affinity of 2×10$^9$ L/mol. The numerical ratio of free antigen to initial antigen is listed below the chart for each initial antigen concentration. As shown in FIG. 2, the percentage of free antigen to total antigen is expected to be a constant 3.23% when the total antigen concentration is at the low end of the range, i.e., over the range 0.05 to 50×10$^{-12}$ mol/L. This contrasts with the conditions expected at initial antigen concentrations higher than 50,000×10$^{-12}$ mol/L, where the presence of the soluble antibody causes more of an offset effect than a scaling effect, as discussed further below.

Within the scalar region at the low range of initial antigen concentration, the concentration of free antibody can be treated as a constant, and Equation (1) can be rewritten:

$$K_a \cdot [Ab_i] \approx K_a \cdot [Ab] = \frac{[AbAg]}{[Ag]} \quad (5)$$

It follows from Equation (5) that when the free antibody concentration is constant, the ratio of bound antigen to free antigen is also constant. This means that when the scaling antibody concentration is much higher than the antigen concentration, the net effect is to reduce the antigen concentration by a constant scale factor. This relationship is exploited by the method of the invention to adjust the equilibrium concentration of free antigen to within the working range of the assay. This is illustrated by the hypothetical reaction conditions used in FIG. 2, where, at an initial antigen concentration of 5×10$^{-12}$ mol/L, equilibrium concentrations of 4.84×10$^{-12}$ mol/L [AgAb] complex, 0.16×10$^{-12}$ mol/L free antigen, and 15×10$^{-9}$ mol/L free scaling antibody would result, a percentage of free antigen of about 3.23%. This in turn results in a constant ratio of initial antigen to free antigen at equilibrium (defined here as α) of about 31:1 over the low end of the range of initial antigen concentrations, and is referred to herein as a scalar constant of 31.

The relationship between the initial antigen concentration and the initial concentration of scaling agent can be derived from Equation (1). First, Equation (3) is rearranged to get:

$$[Ab] = [Ab_i] - [Ab + Ag] \quad (6)$$

Substituting into Equation (1) and rearranging yields:

$$\frac{[Ab + Ag]}{[Ag]} = \frac{K_a \cdot [Ab_i]}{K_a \cdot [Ag] + 1} \quad (7)$$

Adding one to both sides and inverting yields:

$$\frac{[Ag]}{[Ab + Ag] + [Ag]} = \frac{[Ag]}{[Ag_i]} = \frac{K_a \cdot [Ag] + 1}{K_a \cdot [Ab_i] + K_a \cdot [Ag] + 1} \quad (8)$$

Equation (8) defines the ratio of free antigen to total antigen (1/α) in terms of the initial antibody concentration and the free antigen concentration. The left hand side of Equation (8) is the fraction of total antigen concentration that remains free at equilibrium. The right hand side of the equation indicates a dependence on antibody affinity, initial antibody concentration, and equilibrium antigen concentration.

Figure 3:
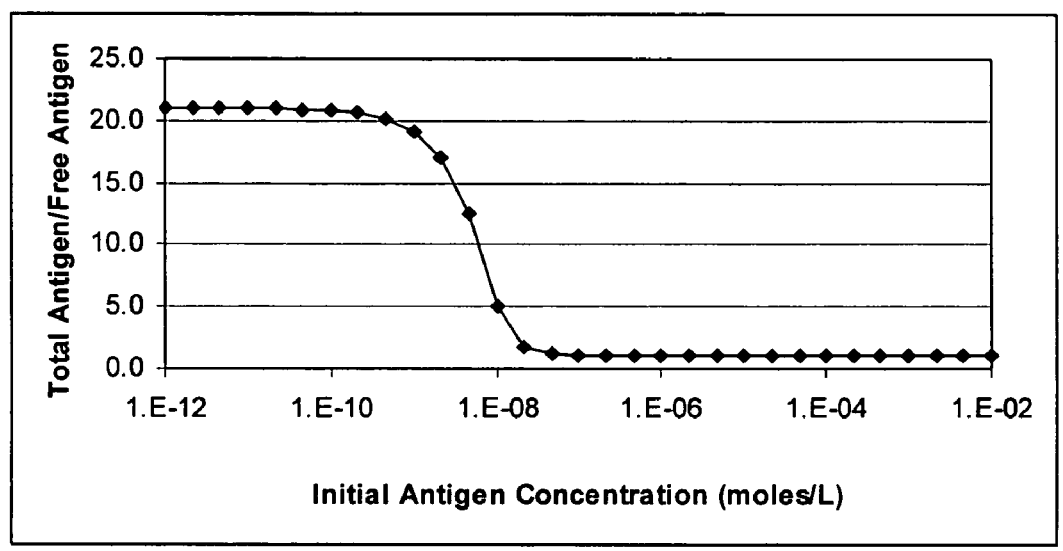
FIG. 3 is a logarithmic plot showing the ratio ($\alpha$) of initial antigen to free antigen over a range of initial antigen concentrations ($10^{-12}$ to $10^{-2}$ mol/L), in the presence of $10 \times 10^{-9}$ mol/L of a scaling antibody having a binding affinity of $2 \times 10^9$ mol/L.

Examining the equilibrium relationship expressed in Equation (1) further suggests that when a high concentration of soluble scaling antibody is mixed with a sample having a relatively low concentration of antigen, a large proportion of the antigen will complex and no longer be available for detection by the capture agent. Due to the nature of the equilibrium between association and dissociation of the antibody/antigen complex, however, a finite portion of the antigen remains present in solution as free antigen. The ratio of the initial antigen concentration to the concentration of free antigen at equilibrium (α) is a useful parameter for modeling the effect of soluble antibody on the concentration of free antigen over a wide range of initial antigen concentrations. FIG. 3 is a graphical plot of α versus initial antigen concentration (10$^{-12}$ to 10$^{-2}$ mol/L) in the presence of 10$^{-8}$ mol/L soluble antibody having a binding affinity of 2×10$^9$ L/mol.

Figure 4:
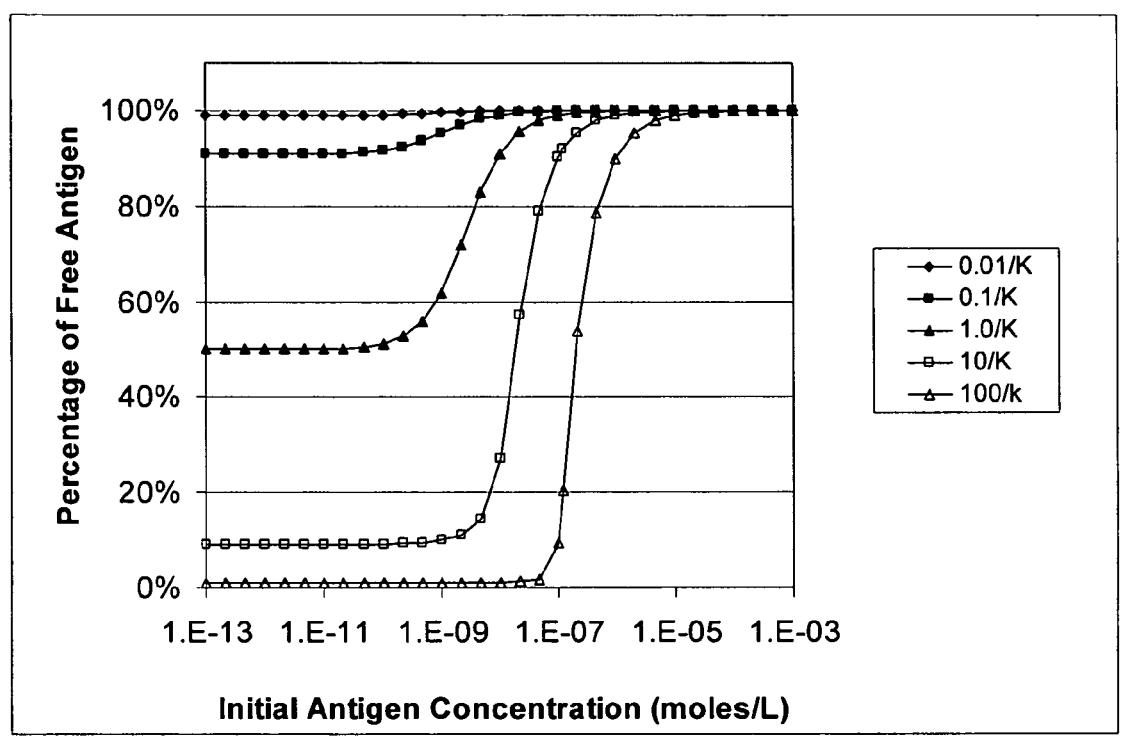
FIG. 4 is a graph showing the percentage of total antigen that remains free at equilibrium for a scaling antibody affinity ($K_a$) of $10^9$ L/mol, at scaling antibody concentrations of $0.01/K_a$ ($10^{-11}$ mol/L), $0.1/K_a$ ($10^{-10}$ mol/L), $1.0/K_a$ ($10^{-9}$ mol/L), $10/K_a$ ($10^{-8}$ mol/L), and $100/K_a$ ($10^{-7}$ mol/L).

This relationship is further explored in FIG. 4, which is a graphical illustration of the percentage of antigen that remains free at equilibrium ($1/\alpha$) over a broad range of initial antigen concentration, shown in the presence of several different concentrations of soluble antibody having a binding affinity of $10^9$ L/mol. As seen in FIG. 4, for each given concentration of soluble antibody, there are three phases to the binding relationship over the range of initial antigen concentrations. The three phases are defined herein as a scalar phase, a transition phase, and an offset phase. The percentage of free antigen is constant over the scalar range (the "scalar constant"), approximates 100% over the offset range, but is highly variable at the transition phase.

(1) Scalar Region

The scalar region is seen on the left side of the graph in the region of relatively low initial antigen concentration, where excess antibody reduces the available antigen concentration by a constant factor, variously referred to herein as the "scalar constant", "scalar coefficient," or "scalar factor." As seen on the left side of the graph in FIG. 4, the percentage of free antigen is depleted by 1% at an antibody concentration of $10^{-11}$ mol/L ($0.01/K_a$), by 10% at an antibody concentration of $10^{-10}$ mol/L ($0.1/K_a$), by 50% at an antibody concentration of $10^{-9}$ mol/L ($1/K_a$), by 90% at an antibody concentration of $10^{-8}$ mol/L ($10/K_a$), and by 99% at an antibody concentration of $10^{-7}$ mol/L ($100/K_a$).

In the scaling region at the far left of the graph shown in FIG. 4, the actual concentration of free antigen is low and can be approximated as, $$[Ag] \Rightarrow 0 \tag{9}$$

In the scalar concentration range in which this simplifying assumption holds true, the portion of antigen that remains free at a given concentration of scaling agent ($1/\alpha$) is calculated according to Equation (8). For the assumption in Equation (9), Equation (8) reduces to:

$$\frac{[Ag]}{[Ag_i]} = \frac{1}{K_a \cdot [Ab_i] + 1} \tag{10}$$

Equations (9) and (10) are valid over the limited range of initial antigen concentrations defined herein as the scaling range.

For relatively low concentrations of antigen, Equation (10) expresses the relationship between the fraction of antigen that is free at equilibrium, initial antibody concentration, and binding affinity. Equation (10) can be used to calculate antigen depletion for a given antibody affinity and antibody concentration.

The ratio ($\alpha$) is defined as the ratio of the initial antigen concentration to the free antigen at equilibrium, and is inversely related to Equation (10):

$$\alpha = \frac{[Ab + Ag] + [Ag]}{[Ag]} = \frac{[Ag_i]}{[Ag]} = K_a \cdot [Ab] + 1 \text{ for } [Ag] \Rightarrow 0 \tag{11}$$

Figure 12:
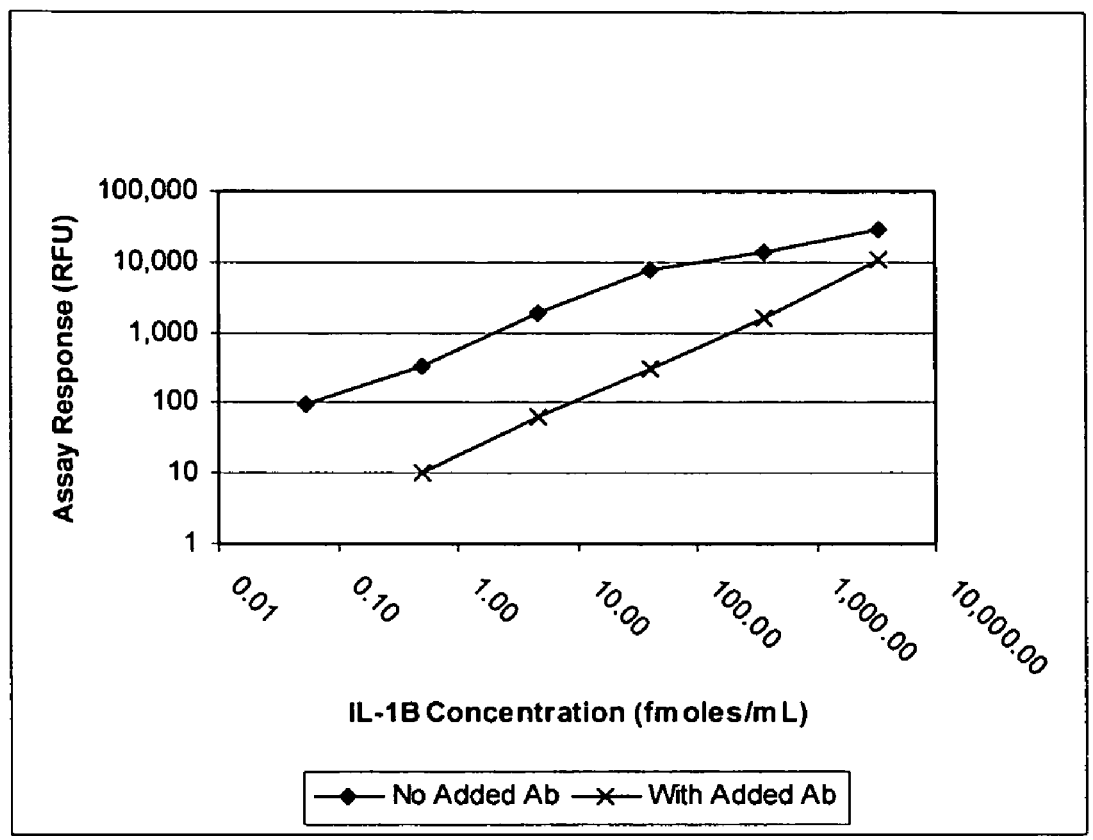
FIG. 12 is a graphical plot of the assay response of an assay for IL-1B analyte, measured as the signal emitted in Relative Fluorescence Units (RFU), in the absence of scaling agent and in the presence of $15 \times 10^{-9}$ mol/L anti-IL-1B antibody as a scaling agent.

The ratio $\alpha$ can be empirically measured by running the same assay with and without a high concentration of scaling agent, as demonstrated by an assay of a sample containing the analyte IL-1B (FIG. 12) with and without scaling agent. FIG. 12 is a graphical representation of the assay response, measured as the signal emitted in Relative Fluorescence Units (RFU), in the absence of scaling agent and in the presence of $15 \times 10^{-9}$ mol/L anti-IL-1B antibody as a scaling agent. The ratio between the signal measured with no scaling agent to the signal emitted in the presence of $15 \times 10^{-9}$ mol/L scaling agent, at IL-1B concentrations of $0.5 \times 10^{-12}$ mol/L and $5 \times 10^{-12}$ mol/L, is about 31, indicating a scaling factor ($\alpha$) of about 31.

For concentrations of soluble antibody larger than the concentration of initial antigen, the scaling constant $\alpha$ is only a function of antibody concentration and affinity. For any given affinity, the scalar constant is determined independent of antigen concentration by choosing an antibody concentration. Within the scaling region, the coefficient $\alpha$ is thus determined solely by the concentration of the scaling agent and the binding affinity of the scaling agent for the analyte. For the example shown in FIG. 3, the binding affinity of the scaling antibody times the concentration of scaling antibody equals 20, and the scale factor is a constant of 21.

FIG. 4 further illustrates that having a high level of antibody concentration relative to that of the antigen will not necessarily cause excessive antigen depletion. On the left hand side of the graph the scaling antibodies are far in excess of the antigen, yet the level of antigen depletion can be quite modest, as is the case for antibody concentrations of 0.01/K.

(2) Offset Region

At antigen concentrations that are higher than the antibody concentrations, the right hand side of Equation (8) approaches one. A high concentration of antigen relative to antibody results in little antigen depletion on a percentage basis (see FIG. 4, right-hand side). There is, however, a constant offset between the initial antigen concentration and the equilibrium antigen concentration for this case.

Referring again to FIG. 4, the offset phase is seen on the right side of the graph in the region of relatively high initial antigen concentrations. In the offset region, the presence of low amounts of soluble antibody produce a simple offset in the concentration of free antigen, the extent of the offset defined by an "offset concentration".

As discussed above, many lateral flow immunoassays are simple tests that provide qualitative positive/negative test results, and frequently are designed to provide a qualitative indication that an analyte is present in a sample only when the analyte is present above a threshold level. The assay response exhibits a relatively abrupt transition from below the threshold concentration to above it. A sharp response allows a well-defined delineation between the presence and lack of a specific analyte. On occasion, such assays exhibit a sharp transition close to, but not precisely at, the threshold of interest. If the transition occurs at a slightly lower antigen concentration than desired, then the assay developer can add a small amount of antibodies to the sample to reduce the amount of available antigen by a fixed amount, which is referred to herein as an "offset" of the concentration of antigen in the sample. For example, the assays disclosed in U.S. Pat. No. 5,541,069 and U.S. Pat. No. 5,780,308 involve adding a low concentration of soluble antibody to a sample to effectively offset the concentration of antigen by a specific amount. There is only a small, defined amount of antibody, so the majority of the antibody forms a complex with antigen, thereby blocking the antigen from detection by the assay. The result is that a fixed amount of antigen is "soaked up", effectively removing antigen from the assay. This has been variously referred to as "blocking", "scavenging", or "sequestering" the analyte. The offset model of the prior art ignores the equilibrium state of association and dissociation between the antibody and the antigen in solution.

Once again Equation (4) is used to further examine the solution conditions when offsetting antigen levels with small amounts of antibody. An offset in the antigen concentration is created by adding a small amount of antibody to the sample to "soak up" a fraction of the antigen. Referring to the assay illustrated in the graph in FIG. 5, the resulting available antigen is calculated over a range of initial antigen concentrations of 5-115 pmol/mL in an assay designed to detect analyte at a concentration of 65 pmol/mL or higher, and with a sharp transition at 50 pmol/mL. If $15 \times 10^{-9}$ mol/L of a soluble antibody with a binding affinity of $2 \times 10^9$ L/mol is added to the sample, the antigen concentration available for detection should be reduced by approximately $15 \times 10^{-9}$ mol/L. The data below the chart in FIG. 5 details the actual variations from the ideal case which are negligible at the threshold. At the threshold concentration of $65 \times 10^{-9}$ mol/L, the available antigen is $50 \times 10^{-9}$ mol/L, which is the assay threshold.

Figure 5:
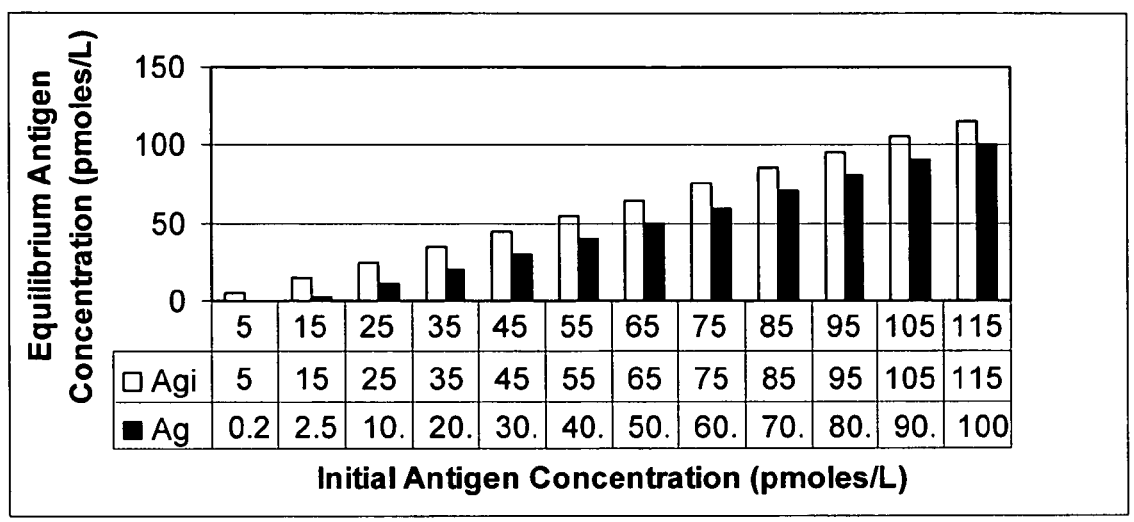
FIG. 5 is a bar graph comparing the ratio of initial antigen to free antigen at equilibrium in the offset range. The available antigen is offset by $15 \times 10^{-9}$ mol/L. The numerical values of initial and free antigen are listed below the bar graph.

The offset effect illustrated in FIG. 5 assumes a lack of dissociation, so the residual free antibody concentration is negligible compared to the original $15 \times 10^{-9}$ mol/L, and the antigen concentration is offset by approximately $15 \times 10^{-9}$ mol/L, which corresponds to the limiting amount of antibody. Therefore, when the added antibody concentration is significantly lower than the antigen concentration, the effect is to offset the available antigen level by a fixed amount.

Figure 6:
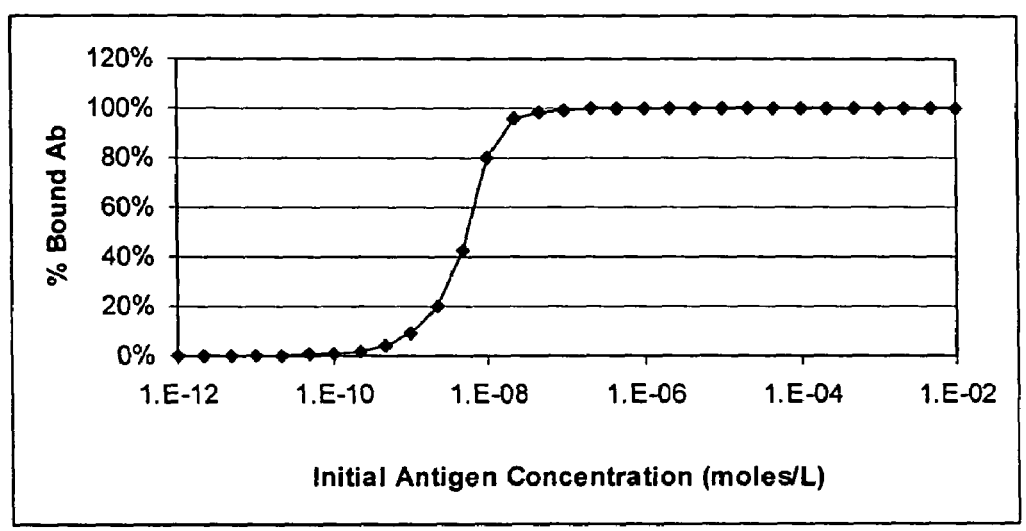
FIG. 6 is a plot of the percent of scaling antibody that is bound to antigen at equilibrium versus initial antigen concentration (range $10^{-12}$ to $10^{-2}$ mol/L), in the presence of a constant amount of a scaling antibody ($10 \times 10^{-9}$ mol/L) having a binding affinity of $2 \times 10^{-9}$ mol/L.
Figure 7:
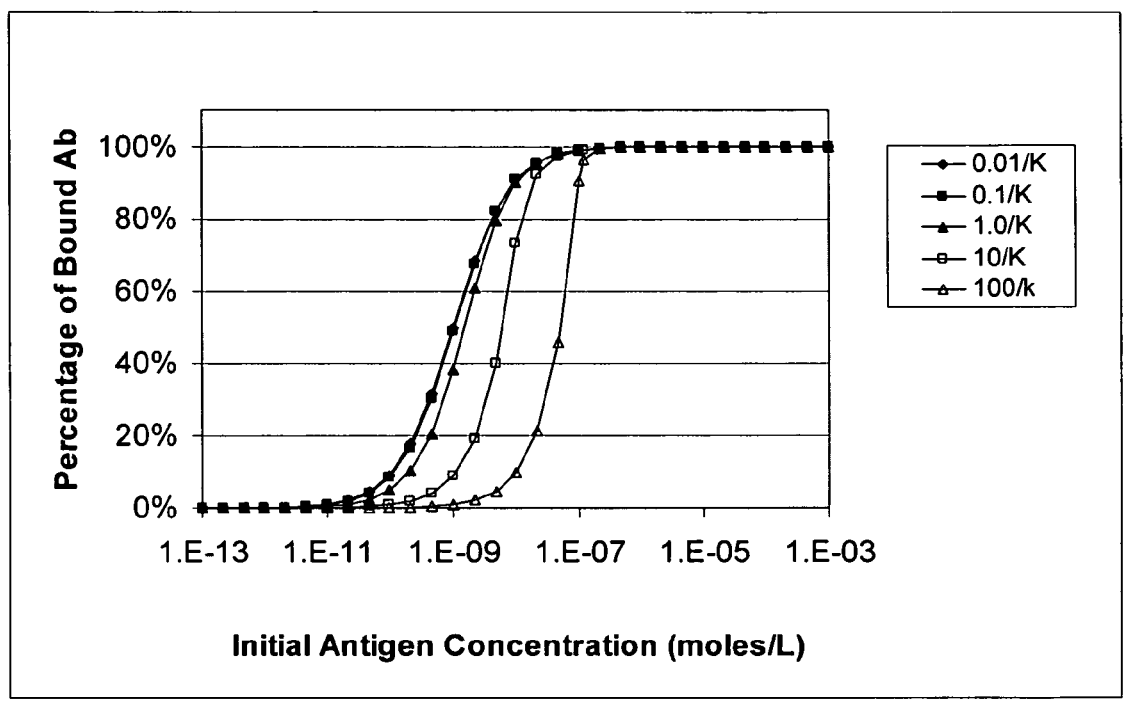
FIG. 7 is a logarithmic graph showing the amount of scaling antibody that is bound as a percentage of the maximum amount of antibody/antigen complex that could be formed given the total amount of scaling antibody present, for each of five different scaling antibody concentrations. The antibody concentrations are $10^{-11}$ mol/L ($0.01/K_a$), $10^{-10}$ mol/L ($0.1/K_a$), $10^{-9}$ mol/L ($1/K_a$), $10^{-8}$ mol/L ($10/K_a$), and $10^{-7}$ mol/L ($100/K_a$).

Within the offset range, the concentration of bound Ag at equilibrium is equal to the difference between the initial and final antigen concentration (FIG. 6). At low initial antigen concentrations, relatively little antigen is bound to antibody, largely because there is very little antigen relative to antibody to begin with. In the mid-range of initial antigen concentrations, a transition develops as the amount of bound antigen concentration begins to rise. At high initial antigen concentrations, the amount of bound antigen becomes constant, indicating a constant offset between the initial and final antigen concentrations.

The use of soluble antibodies by prior art offset assays can be more easily visualized by graphing the offset between the initial antigen level and the antigen level after the antibodies are added. The development of the offset as a function of increasing antigen concentration can be calculated by subtracting the equilibrium concentration from the original concentration over the assay range.

(3) Scalar to Offset Transition

Between the scalar phase and the offset phase is a transition phase, in the mid-range of initial antigen concentrations, where the presence of soluble antibody causes the percentage of free antigen to change rapidly. There are two criteria with which to define the limits between the Scalar and Offset regions. One is suggested by Equation (10) while the other is best illustrated graphically.

The boundary between the scaling region and the offset range can be defined by Equations (8), (9) and (10). The approximation of Equation (9) can be further clarified by considering the numerator and denominator of Equation (8) separately. For the approximation to hold true in the numerator, the product of the binding affinity, $K_a$, and the equilibrium antigen concentration must be less than one fourth, and preferably less than one tenth. For the approximation to hold true in the denominator, the initial antibody concentration must be at least four times, preferably ten times, the equilibrium antigen concentration over the expected assay range. This is summed up in the following equations:

$$\frac{[Ag]}{[Ag_i]} = \frac{K_a \cdot [Ag] + 1}{K_a \cdot [Ab_i] + K_a \cdot [Ag] + 1} \approx \frac{1}{K_a \cdot [Ab_i] + 1} \quad (12)$$

for $$K_a \cdot [Ag] < \frac{1}{4} \quad (13)$$

and $$[Ab_i] > 4 \cdot [Ag] \quad (14)$$

If the conditions of Equations (13) and (14) hold true, then the resulting assay can be said to be operating within the constant scaling range of the assay.

Figure 8:
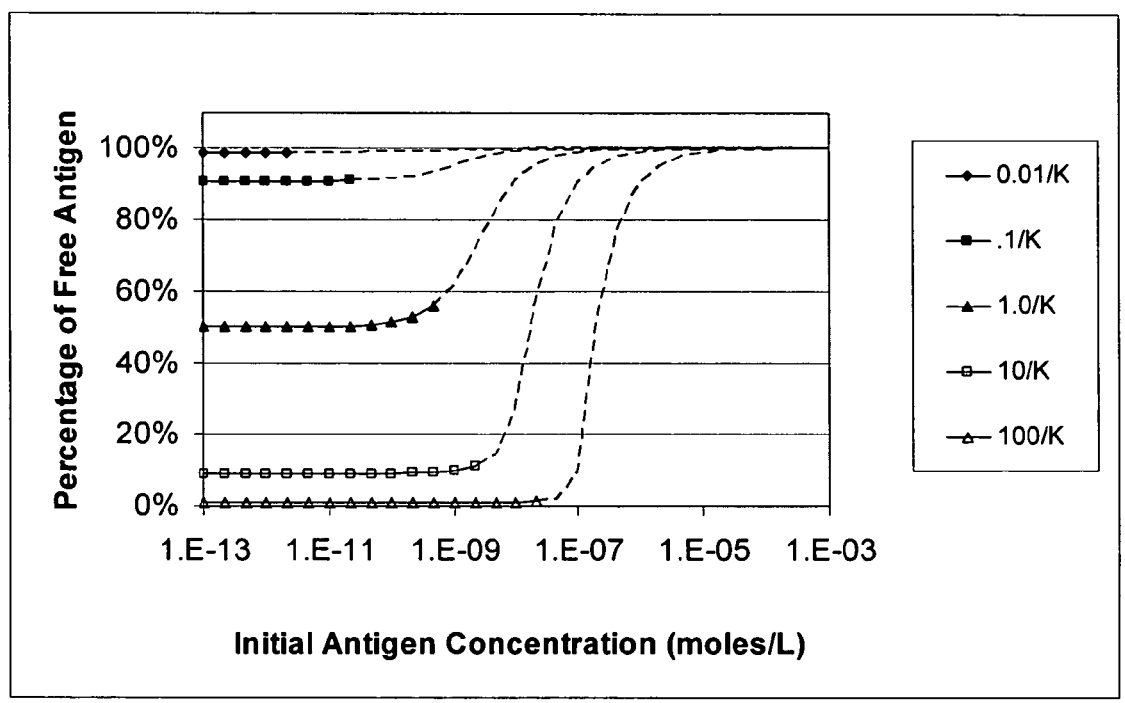
FIG. 8 is a logarithmic graph showing the percent of antigen that is free antigen at equilibrium versus initial antigen concentration (range $10^{-13}$ to $10^{-3}$ mol/L) for each of five different scaling antibody concentrations. The scaling antibody concentrations are $10^{-11}$ mol/L ($0.01/K_a$), $10^{-10}$ mol/L ($0.1/K_a$), $10^{-9}$ mol/L ($1/K_a$), $10^{-8}$ mol/L ($10/K_a$), and $10^{-7}$ mol/L ($100/K_a$). The region of each curve shown as a dotted line corresponds to the antigen range over which the antibody concentration is less than four times that of the free antigen concentration at equilibrium, or over which the product of the antibody affinity and the equilibrium antigen concentration is more than one fourth. The antibody affinity is $10^9$ L/mol.
Figure 9:
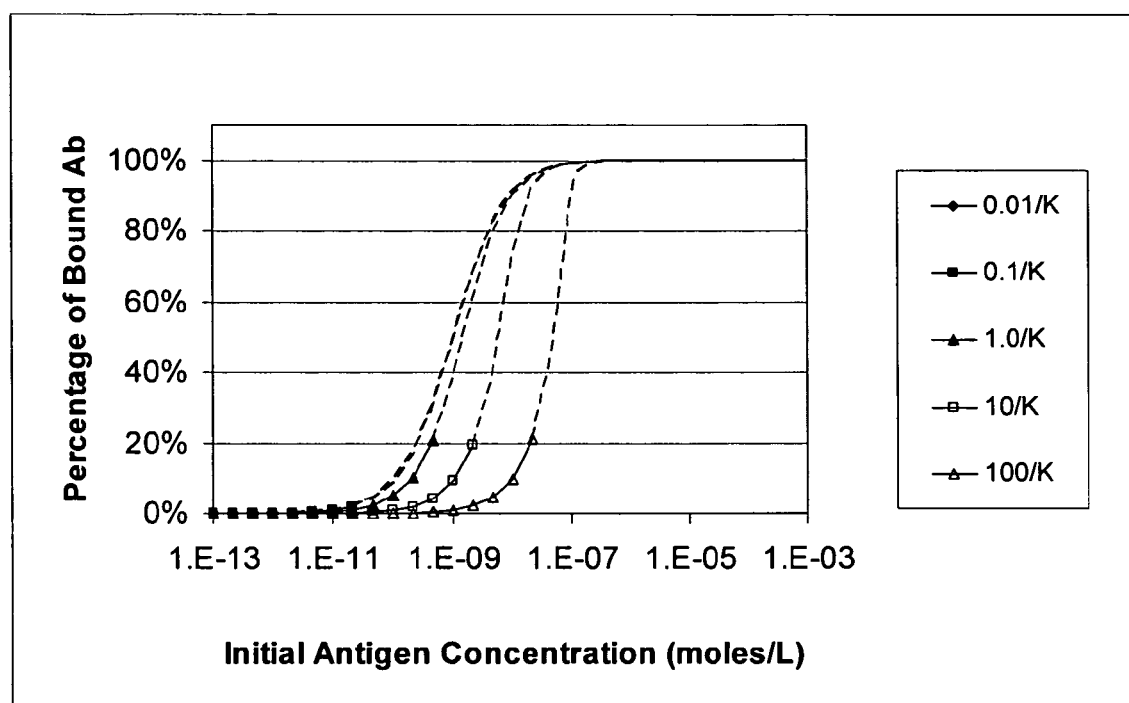
FIG. 9 is a logarithmic graph showing the offset amount of scaling antibody that is bound as a percentage of the maximum amount of antibody/antigen complex that could be formed given the total amount of offset antibody present, for each of five different offset antibody concentrations. The offset antibody concentrations are $10^{-11}$ mol/L ($0.01/K_a$), $10^{-10}$ mol/L ($0.1/K_a$), $10^{-9}$ mol/L ($1/K_a$), $10^{-8}$ mol/L ($10/K_a$), and $10^{-7}$ mol/L ($100/K_a$). The region of each curve shown as a dotted line corresponds to the antigen range over which the scaling antibody concentration is less than four times that of the free antigen concentration at equilibrium, or over which the product of the antibody affinity and the equilibrium antigen concentration is more than one fourth. The antibody affinity is $10^9$ L/mol.

The graph in FIG. 8 shows the same curves as FIG. 4, except that the ranges of antigen concentrations defined by Equations (13) and (14) are identified by solid lines, indicating the range of concentrations over which the invention is being practiced. This scaling assay range is limited to the conditions illustrated on the left side of the graph, in contrast to prior art offset assays which are practiced on the right side of the graph. The visualization is extended in FIG. 9, which shows that the scaling regions remain to the left of the 25% of full offset level.

Figure 10:
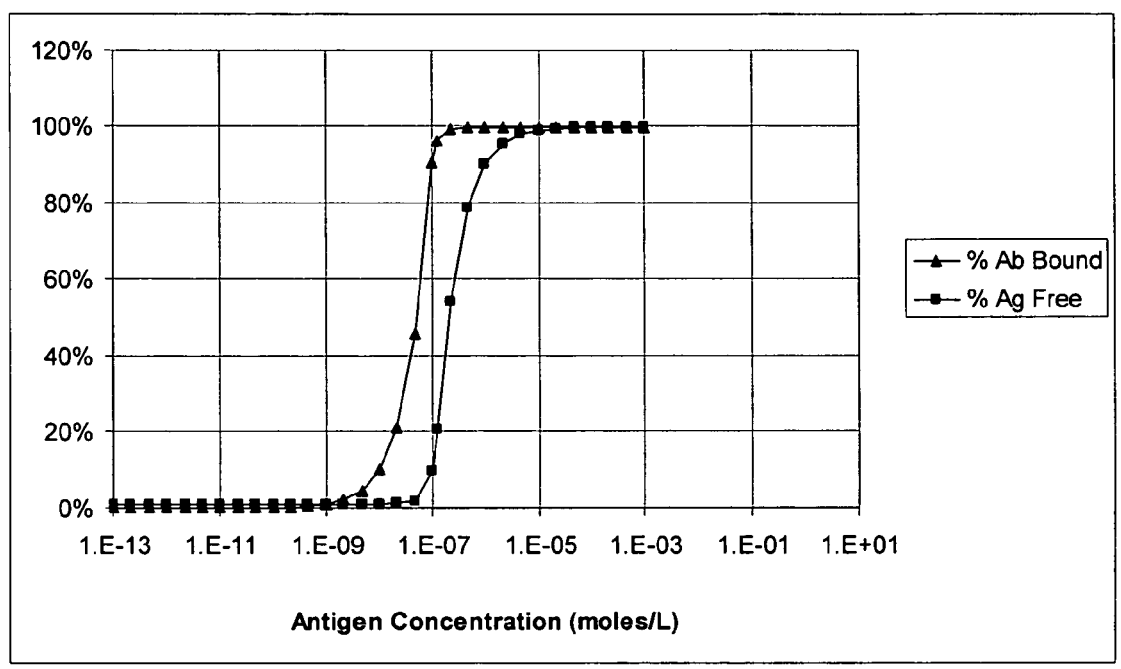
FIG. 10 is a diagram illustrating the scaling effect of FIG. 4 in juxtaposition with the offset effect of FIG. 7, for an antibody affinity of $10^9$ L/mol and an antibody concentration of $10^7$ mol/L.
Figure 11:
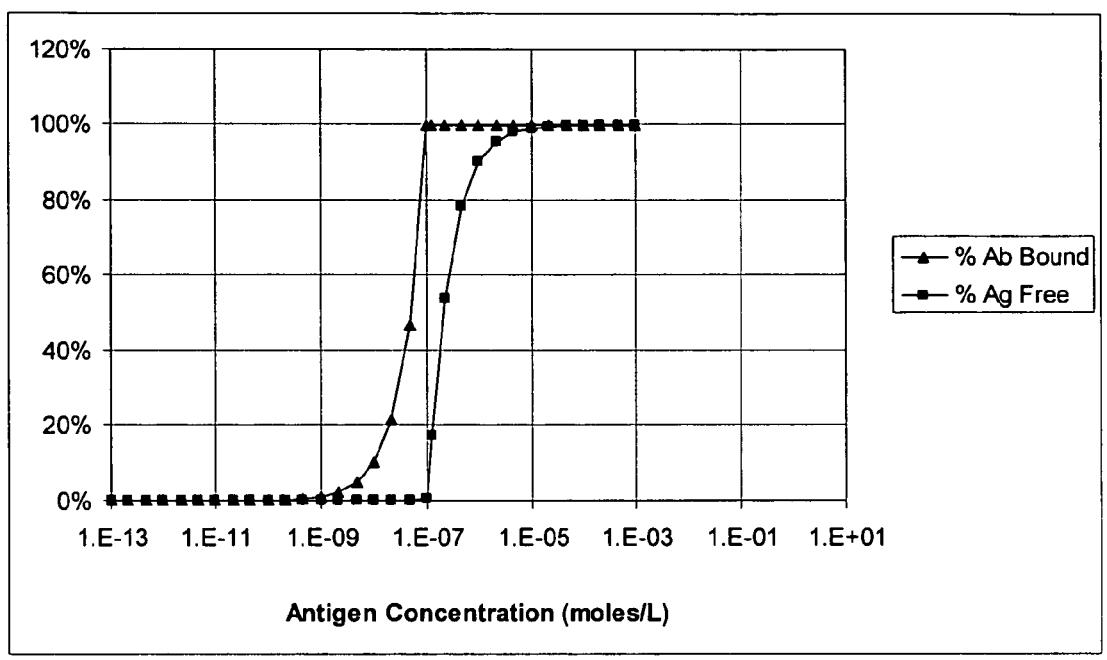
FIG. 11 is a diagram illustrating the scaling effect of FIG. 8 in juxtaposition with the offset effect of FIG. 9, for an antibody affinity of $10^{12}$ L/mol and an antibody concentration of $10^{-7}$ mol/L.

A second criterion by which to delineate scaling effects from offset effects is easily illustrated by viewing the scalar and offset curves on the same graph. In FIG. 10, the curves of the scalar and offset calculations are viewed on a single graph, for the case of a scaling antibody affinity of $10^9$ L/mol and scaling antibody concentration of $10^{-7}$ mol/L. The scaling function loses fidelity before the offset achieves 100%. This is drawn in starker relief for a scaling antibody having a higher binding affinity of $10^{12}$ mol/L (FIG. 11).

The loss of scaling fidelity and the attainment of 100% offset are asymptotically approaching the same concentration for arbitrarily high antibody affinities. The limiting point is the initial antibody concentration. This suggests that the expected initial antigen concentration range relative to initial antibody concentration can be used to differentiate the scalar region from the offset region. Specifically, for initial antigen concentrations lower than the initial antibody range, the analyte concentration is scaled. For an initial antigen concentration that exceeds the initial antibody concentration, the analyte concentration is offset.

This is logically consistent with the workings of the assay. For an arbitrarily high binding affinity, all of the antibodies will complex with any available antigen. Therefore, the attainment of 100% offset will occur exactly when the antigen concentration equals the antibody concentration. Offset assays exceed this level, and therefore are practiced at initial antigen concentration ranges that exceed the initial antibody concentrations. The present invention, on the other hand, relies on the presence of a small, constant concentration of antigen. For arbitrarily high binding affinities, the consistency of the free antigen concentration (as a percentage of the total antigen concentration) loses fidelity at a concentration no higher than the initial antibody concentration. Therefore, the present invention anticipates an antigen concentration range that is always lower than the initial antibody concentration.

In general terms, it can be predicted that assays with a total antigen concentration range at or below the scaling antibody concentration operate in the scaling range, and those that have expected antigen concentrations above the antibody concentration operate in the offset domain. In other words, the full range of the "offset" assay extends well beyond the point at which the offset takes effect.

(4) Measuring Antibody Affinity

Equation (11) can be used to measure the affinity of an antibody from comparative assay data. If the scaling factor is determined experimentally at conditions of excess antibody, then the antibody affinity constant, $K_a$, can be calculated from Equation (15).

$$\alpha = \frac{[Ag_i]}{[Ag]} = K_a \cdot [Ab_i] + 1 \text{ for } [Ab_i] \gg [Ag_i] \quad (15)$$

As discussed in reference to FIG. 12, the scaling coefficient α can be measured empirically by running the same assay with and without the addition of a high concentration of scaling antibody. According to Equation (15), with a scaling coefficient α of 31 and a concentration of scaling antibody of $15 \times 10^{-9}$ mol/L, the affinity of the scaling antibody for the analyte is measured to be $2 \times 10^9$ L/mol:

$$\alpha = Ka \cdot [Ab] + 1 \quad (16)$$

$$Ka = \frac{\alpha - 1}{[Ab]} = \frac{31 - 1}{15 \times 10^{-9}} = 2 \times 10^9 \quad (17)$$

(5) Antigen Availability vs. Assay Sensitivity

An interesting relationship is found by examining Equation (15). For large scaling ratios, α is roughly proportional to the antibody affinity. In other words, antigen availability is inversely proportional to antibody affinity. When the basic assay response is proportional to antibody affinity, the two effects cancel out. This can be useful for eliminating the effects of variations in scaling antibody affinity on assay response, which would be valuable in maintaining repeatability from batch-to-batch of reagents, or with the same reagents over time.

(6) Adjustment of Scaling Factor for Multiple Epitopes

Those skilled in the art will appreciate that an antigen complexes with an antibody at a particular molecular structure called an epitope, and there may be one or more identical epitopes for a given antigen. The signal resulting from an assay will generally be proportional to the number of available epitopes. One way to reduce the signal of a particular antigen, without affecting the other antigens in the assay, is to block a fraction of available epitopes on the target antigen by introducing an appropriate concentration of scaling agents for that epitope into the sample. The concentration of scaling agent required will be a function of several variables, including the number of epitopes per antigen and the magnitude of sensitivity shift desired.

Commonly, e.g., with high affinity IgG antibodies used as scaling agents in an assay for small molecule analytes (such as hormone metabolites and drugs), the valence of the scaling agent for the analyte is two, while the valence of the analyte for the scaling agent is one, i.e., it is sufficiently small that it presents only one binding site to the scaling antibody.

(7) Microarray Technology

When the microarray is exposed to a liquid sample, molecules bound to the spot interact with molecules in the liquid phase. Microarrays that serve as reaction templates for immunoassays are useful for detecting analytes in complex mixtures of proteins. To adapt an immunoassay to a microarray environment, antibodies are used as capture and/or detection agents to quantify the concentration of antigenic proteins in solution matrices such as serum or cell lysates. In the case of sandwich immunoassays, a first antibody ("capture antibody") is immobilized to a solid support, and used to bind a specific antigenic protein in a fluid sample (the "analyte"), and thus remove the analyte from the solution phase. The remaining sample is then washed away and a solution containing a labeling agent, e.g., a detection antibody, is used to label the captured analyte. The detection antibody employs a detectable label as a signaling means (e.g. fluorescence tags) that is either conjugated directly to the antibody or becomes associated with it through an intermediate complex such as biotin/streptavidin.

The capture agent is immobilized to the solid support by methods known to those skilled in the art. Preferably the amount of capture antibody fixed to the solid support is small relative to the amount of sealing agent employed to adjust the linear range of the assay, so that the molar amount of capture antibody need not be accounted for in the equilibrium conditions discussed above.

After the addition of a sample to the microarray, analytes present in the sample bind the specific ligands. The degree of binding is measuring using an optic imager, e.g., a fluorescent imager or a chemiluminescence light reader.

(8) Additional Reaction Formats

Various analytical devices and systems suitable for performing the method of the invention are generally known to those skilled in the art. By way of example, the method of the invention can be used in conjunction with a solution based multiplexed assay, such as that provided by Aclara Biosystems, Inc. (Mountain View, Calif.). The method of the invention is also useful in association with multiplexed assays performed with capture ligands immobilized on a variety of solid supports known to those skilled in the art, such as, without limitation, micro-particles and/or beads, microtiter plates, biochips, planar or semi-planar substrates such as coated slides, lateral flow strips, and various membranes (e.g., cellulose, cellulose nitrate, cellulose acetate, glass fiber, nylon, polyelectrolyte ion exchange membrane, acrylic copolymer/nylon, or polyethersulfone). Examples of such systems include, without limitation, assays conducted in multi-well microtiter plates such as, e.g., SearchLight™ (Pierce Biotechnology, Rockford Ill.), the Multi-Array™, Multi-Spot™, Sensor™ systems (Meso Scale Discovery, a division of Meso Scale Diagnostics LLP, Gaithersburg, Md.) and the A2™ Multiplex Immunoassay using the Biomek® FX laboratory automation workstation (Beckman Coulter, Inc., Fullerton Calif.); assays conducted on or with beads as solid supports, e.g., the XMAP® system (Luminex Corporation, Austin Tex.); immunochromatographic systems based on membranes and/or lateral flow (e.g., RAMP®, Response Biomedical Corporation, Burnaby Calif.); and biochip based systems such as, e.g., the Infinit™ Analyzer and BioFilm-Chip™ microarray system (Autogenomics Inc., Carlsbad, Calif.) and the RX daytona and RX imola systems of Randox Laboratories Ltd (Great Britain). Additional systems that can be used in conjunction with the method of the invention include, e.g., the Stratus CS Analyzer™ of Dade Behring Inc. (Deerfield, Ill.); and systems of Bayer Healthcare Diagnostics Division; and the Triage(r) and Triage(r) Meter Plus systems of Biosite, Inc. (San Diego, Calif.), and the Access® 2 immunoassay systems, SYNCHRON LX®i 725 combination chemistry and immunoassay workstation, and the high throughput UniCel DxI 800 Access immunoassay (Beckman Coulter, Fullerton Calif.).

Suitable signal producing systems include at least one component and may comprise two or more components, including enzymes, substrates, catalysts, enhancers, and the like. In the examples herein, a detection agent is used to label the captured analyte. Usually at least one component of the signal producing system will be, or will be attached to, an agent capable of binding the analyte/capture agent complex, and will thus be bound to the solid phase in the detection phase of the assay of the present invention. Numerous suitable signal producing systems are described in the patent and scientific literature, and will be known to those skilled in the art, e.g., detection labels, imagers, and readers based on fluorescence, radioisotopes, chemiluminescence, colloidal gold, or enzymatic activity, e.g., streptavidin-horseradish peroxidase (SA-HRP). See, e.g., U.S. Pat. Nos. 4,313,734 and 5,529,902, hereby incorporated by reference. The use of a fluorescence producing system that results in attachment of a florescent tag on the solid phase support is preferred. The detection agent employs fluorescent tag, either conjugated directly to the detection agent or attached through an intermediate complex such as biotin/streptavidin. The intensity of the signal resulting from the assay is then quantified using an appropriate imager, e.g., a laser scanning confocal microscope such as a Bio-Rad Lasersharp MRC 500 (Bio-Rad Laboratories Ltd.,). Methods for the adsorption of proteins and protein analogues to colloidal gold are described in, e.g., Leuvering, U.S. Pat. No. 4,313,734, hereby incorporated by reference. Analyte analogue conjugates bearing detectable labels are also well known to those skilled in the art; see, e.g., U.S. Pat. No. 5,851,776, hereby incorporated by reference. Various apparati and devices for, e.g., sample injection, reagent delivery, temperature control, coupling of capture agents to solid supports, reaction mechanics, fluid mechanics, separation technologies, labeling and detection, imaging, calibration, data collection and analysis, are further known to those skilled in the art according to the following references, each of which is hereby incorporated by reference: U.S. Pat. Nos. 6,852,503, 6,638,728, 6,709,743, 6,437,179, 6,040,150, 6,432,662, 5,532,379, 5,538,858, 5,527,688, 5,503,741, 5,266,686, 5,112,952, 5,142,027, and 5,219,528; and US published applications US 2005/0032121, US 2004/0219622, and US 2002/0192736; U.S. Pat. Nos. 6,919,173, 6,242,236, 5,986,811, 5,717,453, 6,319,670, 6,673,533, 6,362,011, and 5,866,434; and US published applications US 2005/0142033, US 2004/00336610, US 2003/0113713, US 2003/0124572, US 2005/0052646, and US 2002/0086335; U.S. Pat. Nos. 6,773,812, 6,916,661, 6,905,766, 6,696,265, 6,649,414, 6,696,304, 6,658,357, 6,592,822, 6,046,807, 6,632,526, and 6,524,793; and US published applications US 2005/0152593, US 2005/0151964, US 2005/0073686, US 2005/0030519, US 2004/0039201, US 2001/0026920, and US 2005/0118574; U.S. Pat. Nos. 6,818,399, 6,673,550, 6,649,351, 6,627,400, 6,306,273, 6,284,113, 6,103,537, 6,103,199, 6,838,680, 6,818,113, 6,614,030, 6,613,525, 6,399,952, and 6,007,690; and US published applications US 2004/0096825, US 2002/0182749, US 2002/0146726, US 2002/0092767, US 2005/0131006, US 2005/0130246, and US 2005/0130238; U.S. Pat. Nos. 6,551,788, 6,867,005, 6,825,041, 6,696,243, 6,740,257, 6,387,672, 6,861,214, 6,843,481, 6,159,749, 6,033,627, 6,387,622, 6,146,833, 5,814,468, 6,110,749, 5,817,468, 6,660,233, 5,882,596, 5,747,352, 5,863,401, 5,571,680, 5,559,012, 5,849,599, 5,447,838, 5,395,754, 5,583,055, 5,371,021, 5,387,527, 5,451,525, 6,168,956, 6,017,767, 5,998,220, 5,877,028, 5,648,274, 5,607,863, 5,468,648, 5,439,829, 5,225,351, 5,296,195, 5,164,311, 5,013,669, 4,788,138, 5,120,504, 5,369,566, 5,139,744, 5,125,748, 5,108,703, 5,104,621, 5,879,881, 4,727,019, 4,595,661, 4,486,530, 4,376,110, and 4,101,276; and US published applications US 2005/0136542, US 2004/0229226, US 2004/0219535, US 2004/0173457, US 2003/0219840, US 2003/0198967, US 2003/0153011, US 2003/0092008, US 2003/0021728, US 2003/0013083, US 2002/0102736, US 2002/0115096, US 2005/0123986, US 2004/0029156, US 2005/0042120, US 2003/0119033, US 2003/0059864, and US 2002/0001853; U.S. Pat. Nos. 5,753,517, 6,509,196 and 6,881,572; and US published applications US 2004/0171092A1, US 2003/0199004A1, US 2003/0071235, and 2003/0162236; U.S. Pat. Nos. 6,341,182, 6,498,010, 6,902,897, 6,897,026, and 6,308,751; and US published applications US 2003/0224447, US 2005/0048672, US 2004/0241700, and US 2003/0071235; US published applications US 2004/0005697, US 2004/0224318, US 2005/0118640, US 2005/0124059, and US 2005/0170356; U.S. Pat. Nos. 6,251,687, 6,830,731, 6,392,894, 6,165,981, 6,121,056, 6,083,708, 5,898,005, 5,861,319, 4,786,606, 4,774,174, 4,752,562, 6,686,208, 6,441,055, 6,440,748, and 6,274,872; and US published application US 2003/0032199; U.S. Pat. Nos. 6,156,270, 6,194,222, 6,391, 265, 6,669,907, 6,297,060, and 6,905,882; and U.S. Pat. No. 5,529,902. Those reagents, devices, and system components disclosed in the above-referenced US patents and published patent applications that are suitable for use with the present invention are recognizable by those skilled in the art, and are each hereby incorporated by reference herein.

EXAMPLE

Results of a multi-analyte assay using the method of the invention are shown in FIGS. 13-16. A set of multiplexed assays of five antigens (IL-1B, IL-2, IL-6, IL-7 & TNFα) were run over an analyte concentration range of 50 pg/ml-500,000 pg/mL. The analyte molar concentrations can be calculated from the molecular weights of the antigens as follows:

| Antigen | Molecular Weight |
|---|---|
| IL-1B | 17 KD |
| IL-2 | 15 KD |
| IL-6 | 20.3 KD |
| IL-7 | 17 KD |
| TNFα | 17.5 KD |

After benchmarking the basic performance of the assays, the IL-1B antigen concentrations were scaled by adding scaling anti-IL-1B. The response to IL-1B was significantly reduced while the others remained substantially unchanged.

Figure 13:
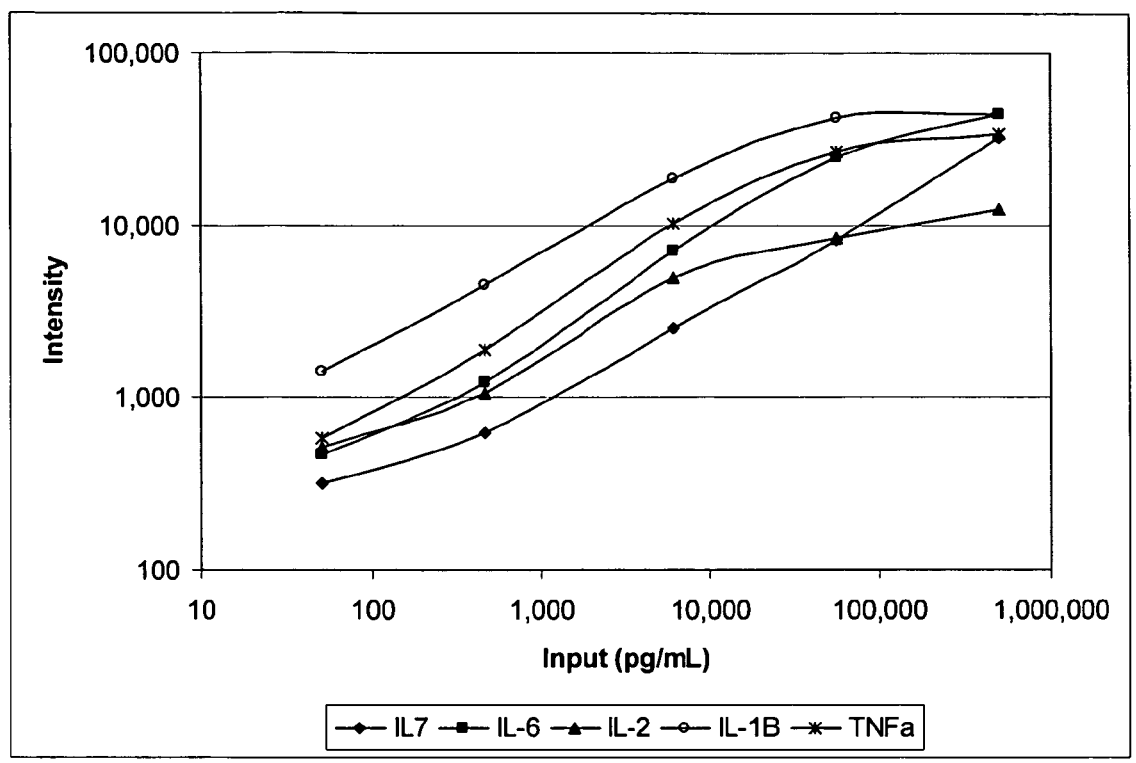
FIG. 13 is a graphical plot of the assay response generated in a multi-analyte assay of five antigens in the absence of scaling agent.

Varied concentrations of five cytokines were spiked into serum and measured using a multiplexed immunoassay. The baseline of the five-plex assay is shown in FIG. 13. The baselines for four of the cytokines assayed (IL-1B, IL-2, IL-6 & TNFα) saturate at the high end of the concentration range. The fifth analyte, the cytokine IL-7, is the only analyte having a linear response out to 500,000 pg/mL. (This may be a function of a low antibody affinity for the IL-7 antibodies.)

Figure 14:
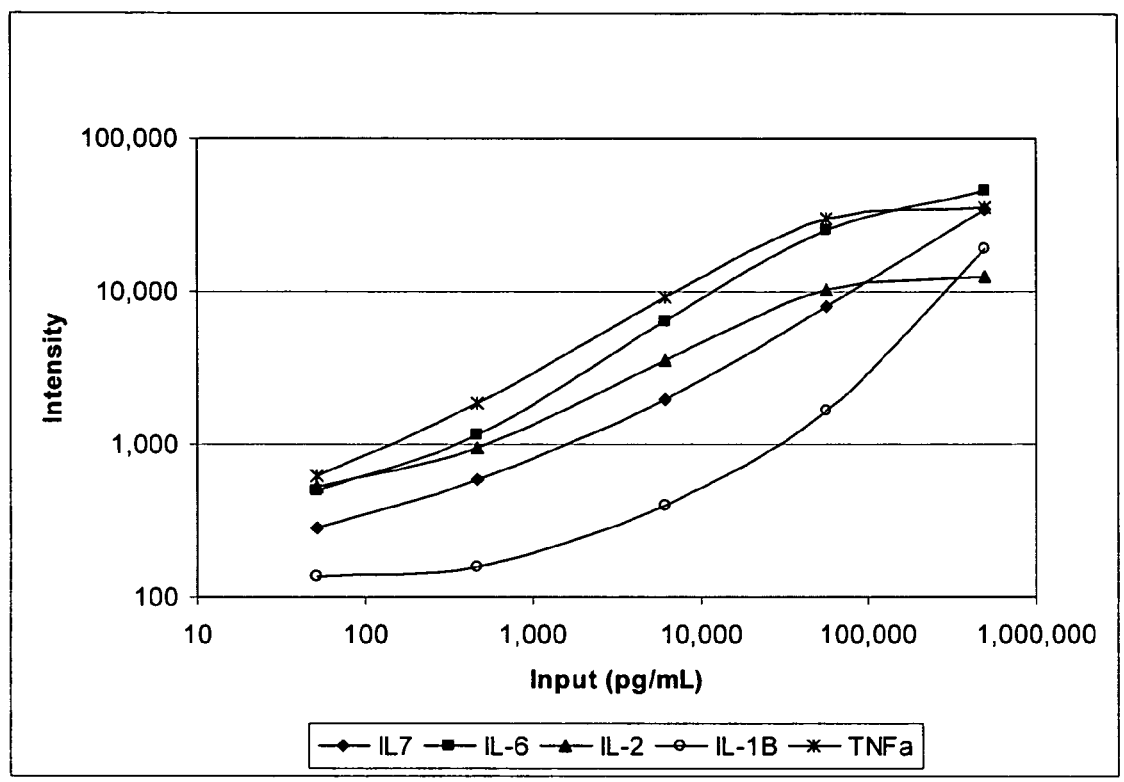
FIG. 14 is a graphical plot of the assay response generated in a multi-analyte assay of five antigens, in the presence of 2.3 pg/mL ($15.2 \times 10^{-9}$ mol/L) of anti-IL-1B antibody as a scaling agent.
Figure 15:
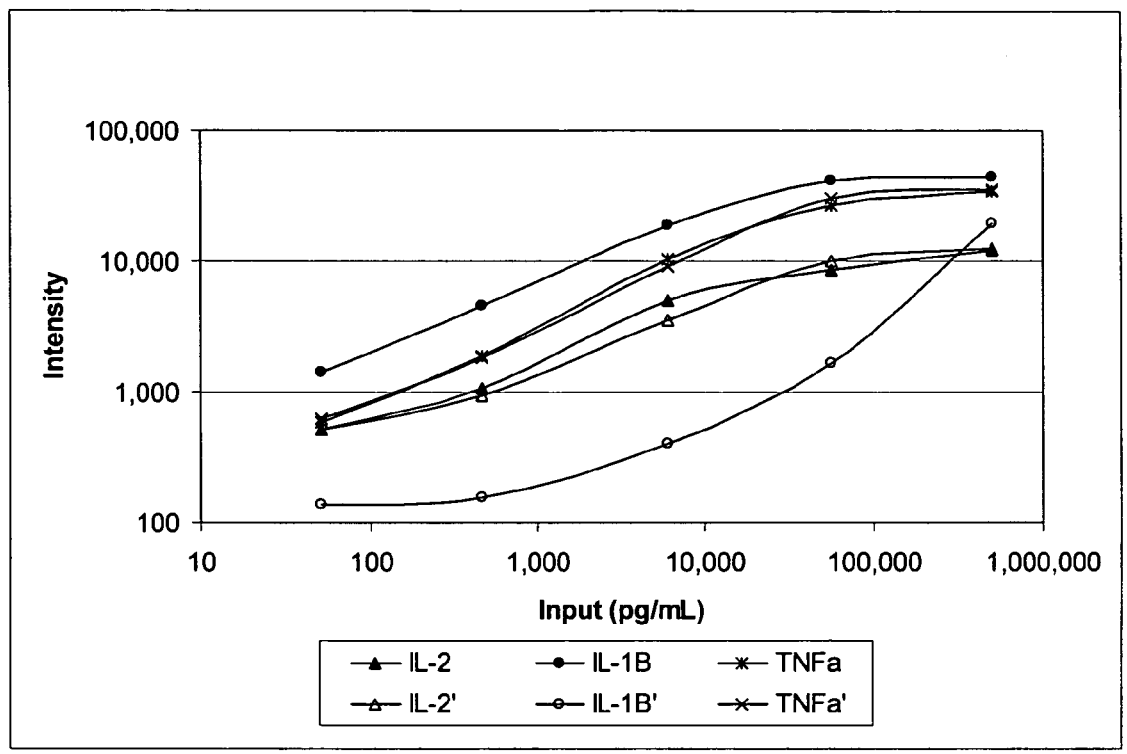
FIG. 15 is a graphical plot of the IL-1B, IL-2, and TNFα curves from FIGS. 13 and 14 superimposed on a single graph.
Figure 16:
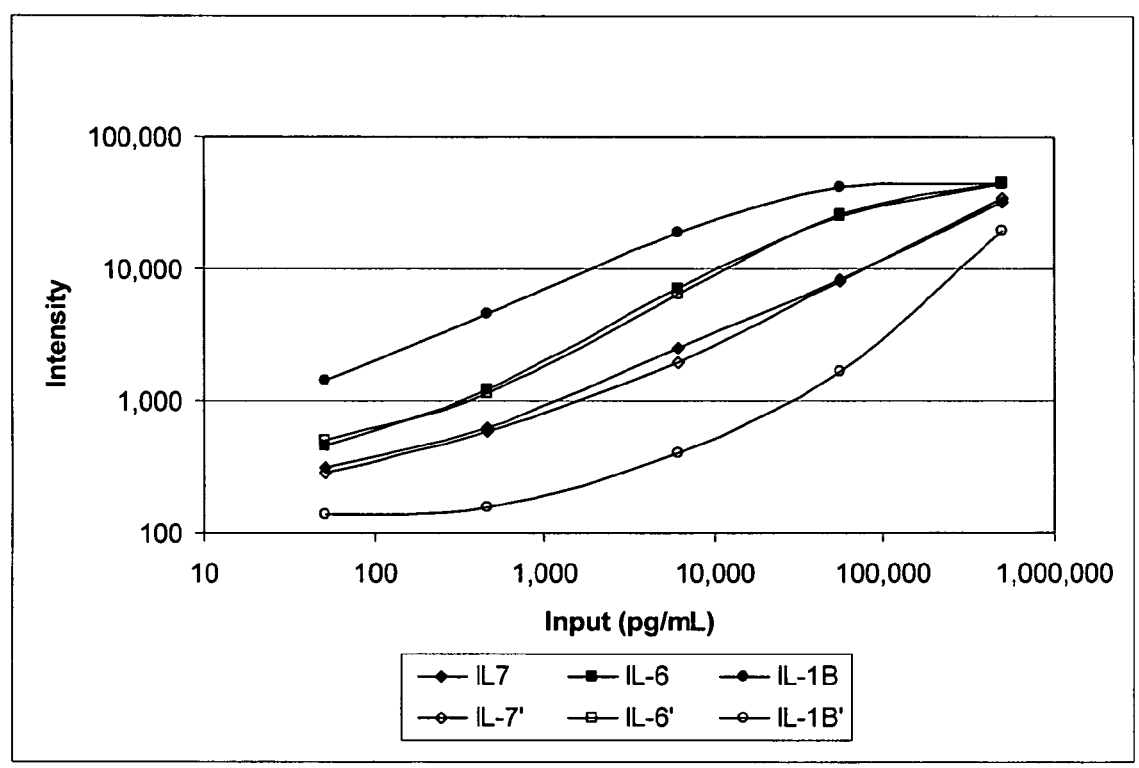
FIG. 16 is a graphical plot of the IL-1B, IL-6, and IL-7 curves from FIGS. 13 and 14 superimposed on a single graph.

In a second set of assays the samples were spiked with 2.3 µg/ml ($15.2 \times 10^{-9}$ mol/L) of IL-1B scaling antibody to scale the concentration of free IL-1B antigen for detection. As shown in FIG. 14, the response of the IL-1B has been reduced by about a factor of 33, while the response to the other cytokines remains unchanged. This is better illustrated in FIGS. 15 and 16. FIG. 15 is a graphical plot of the IL-1B, IL-2, and TNFα curves from FIGS. 13 and 14 superimposed on a single graph. FIG. 16 is a graphical plot of the IL-1B, IL-6, and IL-7 curves from FIGS. 13 and 14 superimposed on a single graph. These two graphs show that the addition of the anti-IL-1B scaling antibody greatly reduces the assay's response to IL-1B, while leaving the response to the other cytokines substantially unchanged.

These data show that multi-analyte assays can be scaled in order to reduce the available concentration of a particular analyte without affecting the response of the other analytes in the system.

The invention claimed is:

1. A method of quantitatively determining the concentration of at least one of a plurality of analytes in a fluid sample, said method comprising:
   a) providing an assay system for quantitatively determining the concentration of a plurality of analytes in a fluid sample, said assay system comprising at least one capture agent immobilized on a solid support, and comprising a defined working range having a high end and a low end;
   b) providing a fluid sample in which each of a plurality of analytes may or may not be present within an expected initial concentration range having a high end and a low end, said plurality of analytes comprising at least one high concentration analyte having a high end expected concentration range that exceeds the high end of said working range of said assay system;
   c) adjusting the expected concentration of said high concentration analyte by a scaling constant, α, so that said high end of said adjusted expected concentration range is less than or equal to the high end of said working range, without adjusting the expected concentration range of at least one other of said plurality of analytes, wherein said adjusting step comprises:
      i) providing a scaling agent (S) having binding specificity for at least one, but not all, of said plurality of analytes, wherein binding of said scaling agent to said high concentration analyte prevents binding of said high concentration analyte to said at least one capture agent; and
      ii) introducing said scaling agent (S) to said sample to create a reaction mixture and allowing the reaction mixture to come to equilibrium, whereby the reaction mixture comprises a scaling agent-analyte complex portion having a scaling agent-analyte complex concentration ([AS]), a free analyte portion having a free analyte concentration ([$A_f$]), and a free scaling agent portion having a free scaling agent concentration ([$S_f$]); wherein said equilibrium reaction mixture comprises a total scaling agent concentration ([$S_T$]) equal to the sum of said free scaling agent concentration plus said scaling agent-analyte complex concentration ([$S_f$]+[AS]), and a total analyte concentration ([$A_T$]) equal to the sum of said free analyte concentration plus said scaling agent-analyte complex concentration ([$A_f$]+[AS]), wherein said scaling agent (S) binds said high concentration analyte with a binding affinity $K_a$, [$S_T$] is greater than [Ar], and the scaling constant, α, is a coefficient proportional to $K_a[S_T]+1$;
   d) subsequent to the reaction mixture coming to equilibrium, introducing at least said free analyte portion of said reaction mixture to a solid support comprising at least one immobilized capture agent, said at least one immobilized capture agent having binding specificity for said high concentration analyte, under conditions permitting binding between said high concentration analyte and said capture agent to form analyte-capture agent complex; and
   e) determining said analyte-capture agent complex on said solid support as an indication of the initial concentration of said high concentration analyte in said fluid sample.

2. The method of claim 1, wherein a ratio of said adjusted concentration of said high concentration analyte to the initial concentration of said high concentration analyte is independent of said initial concentration of said high concentration analyte.

3. The method of claim 1, wherein said total scaling agent concentration ([$S_T$]) is at least four times greater than said free analyte concentration ([$A_f$]), and [$A_f$] $K_a$ is less than one fourth.

4. The method of claim 1, wherein said total scaling agent concentration ([ST]) is at least nine times greater tan said free analyte concentration ([$A_f$]), and [$A_f$] $K_a$ is less than one ninth.

5. The method of claim 1, wherein said scaling constant, α, equals $(K_a[S_T]+1)$.

6. The method of claim 1, wherein [$S_T$] is greater than or equal to [$A_T$] and wherein a ratio of the free analyte concentration to the total analyte concentration, ([$A_f$]/[$A_T$], is independent of said total analyte concentration ([$A_T$]) at said total scaling agent concentration ([$S_T$]).

7. The method of claim 1, wherein a ratio of free analyte concentration to total analyte concentration, ([$A_f$]/[$A_T$], is independent of said total analyte concentration within the adjusted concentration range.

8. The method of claim 1, wherein said determining step comprises measuring a parameter representative of the amount of each analyte bound to said capture agent as an indication of the initial concentration of said analyte in said sample.

9. The method of claim 1, wherein said determining step comprises measuring a detectable signal.

10. The method of claim 1, wherein said determining said analyte-capture agent complex on said solid support comprises introducing at least one detection binder to said solid support under conditions permitting said detection binder to bind said analyte-capture agent complex, and determining the amount of detection binder bound to said analyte-capture agent complex as an indication of the initial concentration of said analytes in said fluid sample.

11. The method of claim 10, wherein said detection binder comprises a detectable signal, and wherein said determining the amount of detection binder bound to said analyte-capture agent complex comprises measuring said detectable signal, said signal being proportional to said concentration of said analyte in said sample.

12. The method of claim 1, wherein said method further comprises the step of removing said scaling agent-analyte complex from said reaction mixture prior to said contacting the reaction mixture with a solid support.

13. The method of claim 1, wherein binding of said scaling agent to said high concentration analyte prevents binding of said high concentration analyte to said at least one capture agent, and wherein said method further comprises the step of, prior to introducing said sample to said solid support, introducing to said reaction mixture an analyte analogue conjugate comprising a detectable signal, said analogue conjugate capable of competing with said high concentration analyte for binding to said scaling agent and said capture agent.

14. The method of claim 13, wherein said determining the amount of each of said analytes bound to said at least one capture agent comprises determining the amount of analyte analogue conjugate bound to said solid support as an inverse indication of the amount of analyte bound to said solid support, and as an inverse indication of the initial concentration of said analytes in said fluid sample.

15. The method of claim 14, wherein said analyte analogue conjugate is present in said reaction mixture at a total analyte analogue conjugate concentration $[A^*_T]$, and said total scaling agent concentration $[S_T]$ is greater than or equal to a sum of said total analyte concentration and said total analyte analogue conjugate concentration $([A_T]+[A^*_T])$.

16. The method of claim 13, wherein said total scaling agent concentration $([S_T])$ is at least four times greater than said free analyte concentration $([A_f])$, and the product of $[A_f]$ and $K_a$ is less than one fourth.

17. The method of claim 13, wherein said total scaling agent concentration $([S_T])$ is at least nine times greater than said free analyte concentration $([A_f])$, and the product of $[A_f]$ and $K_a$ is less than one ninth.

18. The method of claim 1, wherein said step of introducing said free analyte portion of the reaction mixture to the solid support comprises adding the reaction mixture to the solid support.

19. The method of claim 18, wherein said method further comprises the step of removing the scaling agent-analyte complex from the reaction mixture prior to introducing the reaction mixture to the solid support.

* * * * *

UNITED STATES PATENT AND TRADEMARK OFFICE
CERTIFICATE OF CORRECTION

PATENT NO. : 7,396,689 B2 Page 1 of 1
APPLICATION NO. : 11/221198
DATED : July 8, 2008
INVENTOR(S) : Roger Dowd and Jeffrey G. Donahue It is certified that error appears in the above-identified patent and that said Letters Patent is hereby corrected as shown below:

Column 2, line 31, delete "pg/mL" and insert --ng/mL--

Column 9, line 4, delete "$10^7$" and insert --$10^{-7}$--

Column 12, line 65, delete "a" and insert --α--

Column 18, line 20, delete "sealing" and insert --scaling--

Column 21, line 61, delete "[Ar]" and insert --[$A_T$]--

Column 22, line 22, delete "$(K_a[S_T]+1)$" and insert --$(K_a[S_T]+1)$--

Signed and Sealed this

Twenty-eighth Day of October, 2008

JON W. DUDAS
*Director of the United States Patent and Trademark Office*